(12) United States Patent
Xin et al.

(10) Patent No.: US 10,266,840 B2
(45) Date of Patent: Apr. 23, 2019

(54) SORGHUM YIELD ENHANCEMENT GENE

(71) Applicants: The United States of America, as represented by the Secretary of Agriculture, Washington, DC (US); Cold Spring Harbor Laboratory, Cold Spring Harbor, NY (US)

(72) Inventors: Zhanguo Xin, Lubbock, TX (US); Gloria B. Burow, Lubbock, TX (US); Chad M Hayes, Lubbock, TX (US); John J. Burke, Lubbock, TX (US); Doreen Ware, Melville, NY (US); Yinping Jiao, Cold Spring Harbor, NY (US)

(73) Assignees: The United States of America as represented by the Secretary of Agriculture, Washington, DC (US); Cold Spring Harbor Laboratory, Cold Spring Harbor, NY (US)

( * ) Notice: Subject to any disclaimer, the term of this patent is extended or adjusted under 35 U.S.C. 154(b) by 226 days.

(21) Appl. No.: 15/067,641

(22) Filed: Mar. 11, 2016

(65) Prior Publication Data
US 2016/0264986 A1 Sep. 15, 2016

Related U.S. Application Data

(60) Provisional application No. 62/132,574, filed on Mar. 13, 2015.

(51) Int. Cl.
*C12N 15/29* (2006.01)
*C12N 15/82* (2006.01)

(52) U.S. Cl.
CPC ....... *C12N 15/8261* (2013.01); *C12N 15/827* (2013.01); *Y02A 40/146* (2018.01)

(58) Field of Classification Search
None
See application file for complete search history.

(56) References Cited

U.S. PATENT DOCUMENTS

2014/0068798 A1   3/2014   Xin et al.
2016/0289696 A1  10/2016   Xin et al.

OTHER PUBLICATIONS

GenBank Accession EU961498, dated Dec. 10, 2008. (Year: 2008).*
Dixon et al. (The Plant Cell (2018): tpc-00961). (Year: 2018).*
Ramsay et al. (Nature genetics 43.2 (2011): 169). (Year: 2011).*
Ritala et al. (Plant Cell Reports (1993) 12:435-440). (Year: 1993).*
Advanta US, Inc. and USDA/ARS Material Transfer Agreement, signed Mar. 2, 2015 and Feb. 18, 2015.
Amsterdam, Adam et al., "Mutagenesis strategies in zebrafish for identifying genes involved in development and disease", (2006), Trends in Genetics 22(9):473-478.
Ashikari, Motoyuki et al., "Cytokinin Oxidase Regulates Rice Grain Production", (2005) Science 309:741-745.
Bentley, Alyssa et al., "Targeted Recovery of Mutations in *Drosophila*", (2000), Genetics 156:1169-1173.
Brown, P. J. et al., "Inheritance of inflorescence architecture in sorghum", (2006), Theoretical and Applied Genetics 113:931-942.
Burow, Gloria et al., "Multi-Seeded sorghum mutants as a novel trait to boost grain yield (abstract)", First International Conference on Genomics, Traits, and Business,Charlotte, NC, (Sep. 2014), P1:04.
Burow, Gloria et al., "Analysis of Cold Tolerance and "multiseeded" Genetic Stocks of Sorghum", Proceeding of the 2013 SICNA Meeting, (2013) PowerPoint Presentation, 24 slides.
Burow, Gloria et al., "Mutant Resources in Sorghum: Focus on Novel Multiseeded Class", Translational Cereal Genomics Meeting, Vienna, Austria, (2014) PowerPoint Presentation, 16 slides.
Burow, Gloria et al., "Characterization of a Multiseeded (msd1) Mutant of Sorghum for Increasing Grain Yield", (2014), Crop Science 54:1-8.
Burow, G. et al., "Characterization of a multi seeded (msd) mutant of sorghum exhibiting significant enhancement of seed number", Translational Cereal Genomics Meeting, Vienna, Austria, (2014), Abstract.
Chromatin, Inc and USDA/ARS Material Transfer Agreement, signed Oct. 25, 2012.
Duggan, B. L. et al., "Yield component variation in winter wheat grown under drought stress", Canadian Journal of Plant Science, (2000) p. 739-745.
Ejeta, Gebisa and John Axtell, "Mutant gene in sorghum causing leaf "reddening" and increased protein concentration in the grain", Journal of Heredity, (1985) 76:301-302.
Henikoff, Steven et al., "TILLING. Traditional Mutagenesis Meets Functional Genomics", (2004) Plant Physiology 135:630-636.
Monsanto and USDA/ARS Material Transfer Agreement, signed Jan. 13, 2014.
KSU, Agricultural Research Center and USDA/ARS Material Transfer Agreement, signed Oct. 18, 2012.
Nidera USA and USDA/ARS Material Transfer Agreement, signed Oct. 16, 2014 and Nov. 2014.
Oria, Maria P. et al., "A highly digestible sorghum mutant cultivar exhibits a unique folded structure of endosperm protein bodies", (2000) PNAS 97(10):5065-5070.
Paterson, Andrew H., "Genomics of Sorghum", (2008) International Journal of Plant Genomics vol. 2008, Article ID 362451, 6 pages.
Paterson, Andrew H. et al., "The Sorghum bicolor genome and the diversification of grasses", (2009) Nature 457:551-556.
Reynolds, Matthew et al., "Raising yield potential in wheat", (2009) Journal of Experimental Botany 60 (7):1899-1918.
Richards, R.A., "Selectable traits to increase crop photosynthesis and yield of grain crops", (2000) Journal of Experimental Botany 51:447-458.

(Continued)

*Primary Examiner* — Mykola V. Kovalenko
*Assistant Examiner* — Charles Logsdon
(74) *Attorney, Agent, or Firm* — John Fado; Ariel Atkinson

(57) ABSTRACT

The present disclosure provides nucleic acids that confer a multi-seeded phenotype when expressed in plants and uses thereof.

5 Claims, 5 Drawing Sheets
Specification includes a Sequence Listing.

(56) References Cited

OTHER PUBLICATIONS

Saeed, Mohammad et al., "Yield Component Analysis in Grain Sorghum", (1986) Crop Science 26:346-351.
Scott Seed Company and USDA/ARD Material Transfer Agreement, signed Sep. 2012.
Chromatin, Inc. and USDA/ARS Material Transfer Agreement, signed Dec. 15-16, 2014.
Xin, Zhanguo et al., "Multi-seeded sorghum mutants as a Genetic Resource for Enhancing Sorghum yield (abstract)", Sep. 2014.
Keygene N.V. and USDA/ARS Material Transfer Agreement, signed Oct. 29, 2014.
Xin, Zhanguo et al., "SNP-tagged Mutant Library in Sorghum" Poster submission and Abstract for The 2nd Plant Genomics Congress: Asia, Mar. 2015.
Xin, Zhanguo et al., "SNP-tagged Mutant Library in Sorghum" Slide Presentation for The 2nd Plant Genomics Congress: Asia, Mar. 2015, 31 slides.
Nextsteppe, Inc and USDA/ARS Material Transfer Agreement, signed Jan. and Feb. 2012.
Nuseed Americas, Inc. and USDA/ARS Material Transfer Agreement, signed Sep. 28, 2012.
Xin, Zhanguo et al., "Potential of Multiseeded Mutant (msd) to Boost Sorghum Grain Yield", Abstract, Jan. 11, 2015.
Pioneer Hi-Bred International, Inc. and USDA/ARS Material Transfer Agreement, signed Aug. 24, 2011.
Akira, Abe et al., "Genome sequencing reveals agronomically important loci in rice using MutMap", (2012) Nature Biotechnology 30(2):174-179.
Bommert, Peter et al., "Genetics and Evolution of Infloresence and Flower Development in Grasses", (2005) Plant Cell Physiology 46(1):69-78.
Bortiri, Esteban et al., "Flowering and determinacy in maize", (2007) Journal of Experimental Botany 58(5):909-919.
Bortiri, Esteban et al., "ramosa2 Encodes a Lateral Organ Boundary Domain Protein That Determines the Fate of Stem Cells in Branch Meristems of Maize", (2006) The Plant Cell 18:574-585.
Casady, A.J. et al., "Effect of the Twin-seeded Character on Sorghum Performance", (1977) Crop Science 17:117-120.
Cubas, Pilar et al., "The TCP domain: a motif found in proteins regulating plant growth and development", (1999) The Plant Journal 18(2):215-222.

Doebley, John et al., "teosinte branched1 and the Origin of Maize: Evidence for Epistasis and the Evolution of Dominance", (1995) Genetics 141:333-346.
Doebley, John et al., "The evolution of apical dominance in maize", (1997) Nature 386:485-488.
Ikeda, Kyoko et al., "Developmental Course of Infloresence and Spiklet in Rice", (2004) Breeding Science 54:147-156.
Kebrom, Tesfamichael et al., "Vegetative axillary bud dormancy induced by shade and defoliation signals in the grasses", (2010) Plant Signaling & Behavior 5(3):317-319.
Komatsuda, Takao et al., "Six-rowed barley originated from a mutation in a homeodomain-leucine zipper I-class homeobox gene", (2007) PNAS 104(4):1424-1429.
Koppolu, Ravi et al., "Six-rowed spike4 (Vrs4) controls spikelet determinacy and row-type in barley", (2013) PNAS Early Edition 6 pgs.
Kosugi, Shunichi et al., "PCF1 and PCF2 Specifically Bind to cis Elements in the Rice Proliferating Cell Nuclear Antigen Gene", (1997) The Plant Cell 9:1607-1619.
Luo, Da et al., "Origin of floral asymmetry in Antirrhinum", (1995) Nature 383:794-799.
Uberti Manassero, Nora G. et al., "CP transcription factors: architectures of plant form", (2013) BioMol Concepts 4(2):111-127.
Morris, Geoffrey P. et al., "Population genomic and genome-wide association studies of agroclimatic traits in sorghum", (2013) PNAS 110(2):453-458.
Ramsay, Luke et al., "Intermedium-C, a modifier of lateral spikelet fertility in barley, is an ortholog of the maize domestication gene Teosinte Branched 1", (2011) Nature Genetics 43(2):169-173.
Saballos, Ana, "Development and Utilization of Sorghum as a Bioenergy Crop", Vermerris, W. (ed.) (2008) In: Genetic Improvement of Bioenergy Crops, Chapter 8, pp. 211-248, Publisher: Springer.
Takeda, Taito et al., "The OsTB1 gene negatively regulates lateral branching in rice", (2003) The Plant Journal 33:513-520.
Xin, Zhanguo et al., "A high throughput DNA extraction method with high yield and quality", (2012) Plant Methods 8:26 7 pgs.
Xin, Zhanguo et al., "Applying genotyping (TILLING) and phenotyping analyses to elucidate gene function in a chemically induced sorghum mutant population", (2008), BMC Plant Biology 8:103 14 pgs.
Xin, Zhanguo et al., "An Induced Sorghum Mutant Population Suitable for Bioenergy Research", (2009), Bioenergy Res. 2:10-16.
Jiao, Yinping et al., "MSD1 regulates pedicellate spikelet fertility in sorghum through the jasmonic acid pathway", (2018) Nature communication 9:822:1-9; DOI: 10.1038/s41467-018-03238-4.

* cited by examiner

| Crosses | Product | Expected Genetic ratio (and phenotypic %) | SNP KASP assay with ARS1BK_SNP1 | % Identity to Elite Parent |
|---|---|---|---|---|
| msd1-1 × RTX430>>> | F$_1$ | Msd:msd (Phenotype, 100% wild type) | --- | 50% |
| F$_1$ × RTX430>>> | BC$_1$F$_1$ | 1MSDMSD:1Msd:msd (Phenotype, 100% wild type) | Required to select Msd:msd heterozygotes | 75% |
| BC$_1$F$_{1(het)}$ × RTX430>>> | BC$_2$F$_1$ | 1MSDMSD:1Msd:msd (Phenotype, 100% wild type) | Required to select Msd:msd heterozygotes | 87.5% |
| BC$_2$F$_{1(het)}$ × RTX430>>> | BC$_3$F$_1$ | 1MSDMSD:1Msd:msd (Phenotype, 100% wild type) | Required to select Msd:msd heterozygotes | 93.75% |
| BC$_3$F$_{1(het)}$ × RTX430>>> | BC$_4$F$_1$ | 1MSDMSD:1Msd:msd (Phenotype, 100% wild type) | Required to select Msd:msd heterozygotes | 96.87% |
| BC$_4$F$_{1(het)}$ × RTX430>>> | BC$_5$F$_1$ | 1MSDMSD:1Msd:msd (Phenotype, 100% wild type) | Required to select Msd:msd heterozygotes | 98.44% |
| BC$_5$F$_1$×BC$_5$F$_1$ (self pollination) | INBRED | 1MSDMSD:2Msd:msd:1msdmsd (Phenotype:75% wild type:25% multiseeded) | Required to select multiseeded at early seedling stage | ~99% |

FIG. 5

SORGHUM YIELD ENHANCEMENT GENE

FIELD OF THE INVENTION

The disclosure relates to methods for significantly increasing the seed production and yield of grain crop plants.

BACKGROUND OF THE INVENTION

Global demand and consumption of grain crops for food, feed, and fuel is increasing at a rapid pace. This demand has been expanding for many years and is expected to continue increasing as human populations increase.

To meet the constantly increasing demand for grain, producers typically either increase the area under production or attempt to increase the productivity of the grain crop on existing farmland. These two options are not mutually exclusive and both are often employed together. Unfortunately however, the amount of arable land remains limited. Indeed, the acreage available for planting may even decrease as demand for grain increases, since humans have many uses for land in addition to farming. Therefore, cultivating more acres of farmland is not the most desirable way to increase grain yields.

Because the area of land available for farming is limited, increasing productivity of grain crops on existing agricultural land is a laudable goal. Productivity of grain crops on existing agricultural land has been greatly enhanced through the development and widespread use of new farming technologies such as e.g., the use of hybrid grain crops e.g., hybrid corn, hybrid *sorghum*, etc., synthetic fertilizers; and farm machinery. Unfortunately, however, many new farming technologies have environmental consequences such as those associated with increased use of nitrogen fertilizers. Indeed, fertilizer runoff reduces water quality and increases the size of hypoxic zones.

Therefore, what is needed in the art are improved methods for increasing productivity of grain crops which do not require more farmland and which do not damage the environment.

Fortunately, as will be clear from the following disclosure, the present invention provides for these and other needs.

SUMMARY OF THE INVENTION

One exemplary embodiment of the disclosure provides a method for constructing a genetically altered grain crop plant wherein the genetically altered grain crop plant exhibits a multi-seeded phenotype, the method comprising: (i) introducing a heterologous MSD1 nucleic acid into a grain crop plant to provide a genetically altered grain crop plant; (ii) selecting the genetically altered grain crop plant that is homozygous for the heterologous MSD1 nucleic acid, thereby constructing the genetically altered grain crop plant wherein the genetically altered grain crop plant exhibits a multi-seeded phenotype. In one exemplary embodiment, the grain crop plant is a member selected from the group consisting of *sorghum*, barley, rice, maize and wheat. In another exemplary embodiment, the heterologous MSD1 nucleic acid is expressed from a promoter operably linked to the MSD1 nucleic acid. In another exemplary embodiment, the grain crop plant is a member selected from the group consisting of *sorghum*, barley, rice, maize and wheat and wherein the introducing step is achieved by agrobacterium transformation. In another exemplary embodiment, the grain crop plant is a member selected from the group consisting of *sorghum*, barley, rice, maize and wheat and wherein the introducing is achieved by genome editing in another exemplary embodiment, the grain crop plant is *sorghum* and wherein the introducing is achieved by introgression using marker assisted selection. In another exemplary embodiment, the MSD1 nucleic acid is a member selected from the group consisting of SEQ ID NO: 2, SEQ ID NO: 3, SEQ ID NO: 4, SEQ ID NO: 5, SEQ ID NO: 6 SEQ ID NO: 7 and SEQ ID NO: 8, Another exemplary embodiment of the disclosure provides a genetically altered grain crop plant having a multi-seeded phenotype wherein the genetically altered grain crop plant expresses a heterologous MSD1 nucleic acid that is a member selected from the group consisting of SEQ ID NO: 2, SEQ ID NO: 3, SEQ ID NO: 4, SEQ ID NO: 5, SEQ ID NO: 6 SEQ ID NO: 7 and SEQ ID NO: 8. In one exemplary embodiment, the genetically modified grain crop plant is a member selected from the group consisting of *sorghum*, barley, rice, maize and wheat. In another exemplary embodiment, the disclosure provides a seed from the genetically altered grain crop plant wherein the seed comprises a heterologous MSD1 nucleic acid. In another exemplary embodiment, the disclosure provides a genetically altered grain crop plant comprising a heterologous MSD1 nucleic acid or part thereof produced by growing the seed. In another exemplary embodiment, the disclosure provides a tissue culture of regenerable cells produced from the genetically altered grain crop plant having a multi-seeded phenotype. In still another exemplary embodiment, the disclosure provides a protoplast produced from the tissue culture of regenerable cells produced from the genetically altered grain crop plant having a multi-seeded phenotype.

Another exemplary embodiment of the disclosure provides a method for producing *sorghum* cultivars having enhanced grain yield, the method comprising: (i) constructing a *sorghum* cultivar that expresses a heterologous MSD1 nucleic acid by introgression using marker assisted selection, to provide a *sorghum* cultivar having a multi-seeded phenotype, thereby producing *sorghum* cultivars having enhanced grain yield. In one exemplary embodiment, the disclosure provides a seed from the *sorghum* cultivar having enhanced grain yield wherein the seed comprises the heterologous MSD1 nucleic acid. In another exemplary embodiment, the disclosure provides a *sorghum* cultivar having enhanced grain yield or part thereof produced by growing the seed. In another exemplary embodiment, the disclosure provides a tissue culture of regenerable cells produced from the *sorghum* cultivar having enhanced grain yield. In another exemplary embodiment, the disclosure provides a protoplast produced from the tissue culture of regenerable cells produced from the *sorghum* cultivar having enhanced grain yield.

Another exemplary embodiment of the invention is to have a genetically altered grain crop plant having the multi-seeded phenotype (msd) such that the cells of the genetically altered grain crop plant produces a protein having an amino acid sequence selected from the group consisting of SEQ ID NO: 30, SEQ :ID NO: 31, SEQ ID NO: 32, SEQ ID NO: 33, SEQ ID NO: 34, SEQ ID NO: 35, and SEQ ID NO: 36. The genetically altered grain crop plant can be *sorghum*, barley, rice, maize, or wheat. This genetically altered grain crop plant contains a heterologous MSD1 that encodes for the protein having the amino acid sequence of SEQ ID NO: 30, SEQ ID NO: 31, SEQ ID NO: 32, SEQ ID NO: 33, SEQ ID NO: 34, SEQ ID NO: 35, or SEQ ID NO: 36. A seed from this genetically altered grain crop that produces this MSD1 protein is another embodiment of this invention, as is a genetically altered grain crop produced by growing this seed. A cell from this genetically altered grain crop that produces this MSD1 protein, a tissue culture containing the cells from this genetically altered grain crop, and a protoplast containing these cells are additional embodiments of this invention.

Other embodiments of the inventions described herein include kits, and methods of using such kits, that contain at least one pair of polynucleotides which can be used to determine if a plant carries a wild-type Sb07g021140 or a mutated Sb07g021140 (a msd1 mutation) where the mutation is a single nucleotide change. Such kits can optionally include a dye for identifying the SNP, and also instructions for use of the pair of polynucleotides. For mutant p12 (msd1-1), one pair of polynucleotides primers useful for this assay are the two versions of ARSLBK_SNP1 (SEQ ID NO: 9) where G at position 290 is the wild-type sequence and A at position 290 is msd1-1 sequence (see Table 1). Another set of primers for mutant p12 (msd1-1) is in Table 9 and labeled as LBK_ARS_Msd1-1 (SEQ ID NO: 17, SEQ ID NO: 18, and SEQ ID NO: 19). SEQ ID NO: 17 primer is used for identification of wild type plant, SEQ ID NO: 18 primer is designated for identification of mutant p12 plant (msd1-1), and SEQ ID NO: 19 is the common reverse primer for SEQ ID NO: 17 and SEQ ID NO: 18. For mutant p15 (msd1-2), one pair of polynucleotides primers useful for this assay are the two versions of ARSLBK_SNP2 (SEQ ID NO: 10) where C at position 289 is the wild-type sequence and T at position 289 is msd1-2 sequence (see Table 1). Another set of primers for mutant p15 (msd1-2) is in Table 9 and labeled as LBK_ARS_Msd1-2 (SEQ ID NO: 20, SEQ ID NO: 21, and SEQ ID NO: 22). SEQ ID NO: 20 primer is for identification of mutant p15 plant (msd1-2); SEQ ID NO: 21 primer is designated for identification of wild type plant; and SEQ ID NO: 22 is the common reverse primer for SEQ ID NO: 20 and SEQ ID NO: 21. For mutant p18 (msd1-3), one pair of polynucleotides primers useful for this assay are the two versions of ARSLBK_SNP3 (SEQ ID NO: 11) where C at position 368 is the wild-type sequence and T at position 368 is msd1-3 sequence (see Table 1). Another set of primers for mutant p18 (msd1-3) is in Table 9 and labeled as LBK_ARS_Msd1-3 (SEQ ID NO: 23, SEQ ID NO: 24, and SEQ ID NO: 25). SEQ ID NO: 23 primer is for identification of mutant p18 (msd1-3); SEQ ID NO: 24 primer is designated for identification of wild type plant; and SEQ ID NO: 25 is the common reverse primer for SEQ ID NO: 23 and SEQ NO: 24. For mutant p2 (msd1-4), one pair of polynucleotides primers useful for this assay are the two versions of ARSLBK_SNP4 (SEQ ID NO: 12) where C at position 382 is the wild-type sequence and T at position 382 is msd1-4 sequence (see Table 1). Another set of primers for mutant p2 (msd1-4) is in Table 9 and labeled as LBK_ARS_Msd1-4 (SEQ NO: 26, SEQ ID NO: 27, and SEQ ID NO: 28). SEQ ID NO: 26 primer is for identification of mutant p2 (msd1-4); SEQ ID NO: 27 primer is designated for identification of wild type plant; and SEQ ID NO: 28 is the common reverse primer for SEQ ID NO: 23 and SEQ ID NO: 24. For mutant p10 (msd1-5), one pair of polynucleotides primers useful for this assay are the two versions of ARSLBK_SNP5 (SEQ ID NO: 13) where G at position 244 is the wild-type sequence and A at position 244 is msd1-5 sequence (see Table 1). Another set of primers for mutant p10 (msd1-5) is in Table 9 and labeled as LBK_ARS_Msd1-5 (SEQ ID NO: 14, SEQ ID NO: 15, and SEQ ID NO: 16) SEQ ID NO: 14 primer is for identification of mutant p10 (msd1-5); SEQ ID NO: 15 primer is designated for identification of wild type plant; and SEQ ID NO: 16 is the common reverse primer for SEQ ID NO: 14 and SEQ ID NO: 15. During crossing of one genetically altered plant expressing the MSD1 phenotype with a non-genetically altered plant into which one wants to breed and express the MSD1 phenotype; one can use the kit to determine which progeny of the cross contains the desired genetic alteration. Thus, methods of using these kits are also included in the invention.

Other features, objects and advantages of the invention will be apparent from the detailed description that follows.

BRIEF DESCRIPTION OF THE DRAWINGS

FIG. 5 shows a schematic diagram of Marker Assisted Rapid Trait Introgression (MARTI) using for msd1-1 SNP, ARSLBK_SNP1 to elite parent, RTX430 as an example. Simultaneous introgression can be performed through MARTI approach using two or more elite lines of interest to increase throughput. Because of the exceptional time saving via application of specific SNP primers (ARSLBK_SNP1), the whole process greatly accelerated the development of inbred lines to 2-2.5 years as compared to 6 years with conventional approach.

DETAILED DESCRIPTION OF THE INVENTION

Definitions

Figure 1:
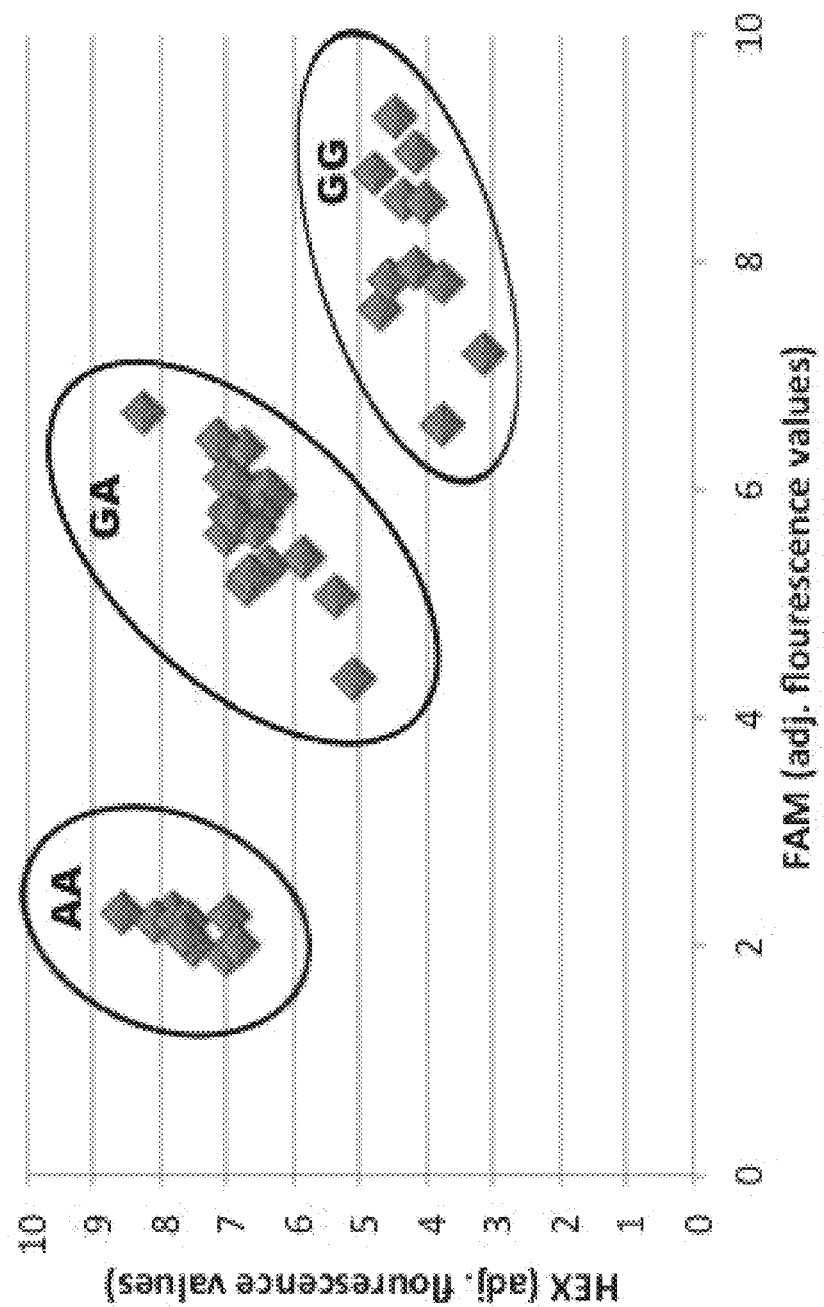
FIG. 1 shows the genotype plots of a $F_2$ breeding population. 48 $F_2$ plants derived from a cross of RTx437 by p12 were genotyped by KASP. AA, homozygous mutants; GA, heterozygotes; and GG, homozygous wild type. The phenotypic ratio was 3 MSD:1 msd and genotypic ratio based on msd1-1 SNP was 1GG:2GA:1AA.

The term "plant" as used herein refers to whole plants, plant bodies, plant organs (e.g., leaves, stems, flowers, roots, etc.), seeds, plant tissues, plant cells and progeny of same. In an exemplary embodiment, a plant cell includes callus. In another exemplary embodiment, a plant organ includes a root, a leaf, a flower, a pollen, a seed, and/or the like. The term "plant" refers to plants of any variety of ploidy levels, including polyploid, diploid, haploid and hemizygous.

The term "grain crop" or "grain plant" as used herein refers generally to plants, which are members of the Poaceae family (grass family). In some exemplary embodiments, members of the Poaceae family produce an edible grain. In other exemplary embodiments, members of the Poaceae family produce grain crops useful as fuel. In still other exemplary embodiments, members of the Poaceae family produce grain crops useful as animal feed, Exemplary grain crops include but are not limited to e.g., *sorghum*, rice, oats, barley, wheat, maize, flax, hops, rye, millet, triticale, etc.

The term "multi-seeded phenotype" or "multi-seeded" or "MSD", as used herein refers to grain crop plants which develop seeds at not only the sessile spikelets of the panicles, but also at the pedicellate spikelets. Thus, grain crop plants having a "multi-seeded phenotype" have pedicellate spikelets that produce mature viable seed.

Wild-type grain crop plants produce a main inflorescence, primary branches, secondary, and tertiary branches, which all end with a terminal spike consisting of one sessile complete spikelet (fertile floret) and two sterile pedicellate spikelets (florets with a pedicel). One or more adjacent spikes may also develop below the terminal spike. The adjacent spikes usually consist of one sessile and one pedicellate spikelet. Typically, in wild-type grain crop plants, only the sessile spikelets of terminal or adjacent spikes are complete flowers that will develop into mature seeds; the pedicellate spikelets are sterile and do not produce mature seed. However, in addition to producing flowers and seed on the sessile spikelet, grain crop plants having a "multi-seeded phenotype" also develop complete flowers on the pedicellate spikelets with full development of functional gynoecium (ovary, style and stigma) and androecium (complete set of 3 anthers with copious amount of pollen). Thus, seed yields per panicle in grain crop plants having a "multi-seeded phenotype" are greatly increased in comparison to normal wild-type grain crop plants, both in number of seeds produced and total seedweight per panicle or plant.

The term "MSD1 nucleic acid" as used herein, refers to a nucleic acid that, when expressed in a plant, e.g., a grain crop plant, confers the multi-seeded phenotype on the grain crop plant in which it is expressed. In exemplary embodiments, the MSD1 nucleic acid that confers the multi-seeded phenotype on the grain crop plant in which it is expressed is present in the grain crop plant in a homozygous condition. In one exemplary embodiment, an MSD1 nucleic acid is operably linked to and expressed from a heterologous promoter. In another exemplary embodiment, the MSD1 nucleic acid is expressed from an expression cassette on an expression vector. Exemplary MSD1 nucleic acids include e.g., SEQ ID NO: 2, SEQ NO: 3, SEQ ID NO: 4, SEQ ID NO: 5, SEQ ID NO: 6 SEQ ID NO: 7 and SEQ ID NO: 8.

The term "promoter" or "promoter complex" or "promoter sequence" as used herein refers to an array of nucleic acid expression control sequences that direct transcription of a nucleic acid. As used herein, a "promoter" or "promoter complex" or "promoter sequence" comprises necessary nucleic acid sequences near the start site of transcription, such as, e.g., a polymerase II type promoter, a TATA element, etc., to "control" transcription of an operably linked nucleic acid. In some exemplary embodiments, a "promoter complex" or "promoter sequence" also includes distal enhancer or repressor elements, which can be, but are not necessarily located as much as several thousand base pairs from the start site of transcription. In other exemplary embodiments, "promoter" or "promoter complex" or "promoter sequence" includes sequences that facilitate transcription of an operably linked heterologous nucleic acid and/or expression of the final protein product of the heterologous nucleic acid, e.g., intron sequence and/or intron and ubiquitin monomer sequences as disclosed herein.

The expression "control transcription", "controlling transcription" or "control of transcription" or other grammatically equivalent phrases or expressions as used herein refers to the ability of an "expression control sequence" typically a promoter, to direct transcription of an operably linked nucleic acid sequence. Methods for testing the activity of promoters and putative promoters in plant cells are known in the art. See, e.g., L. Szabados et al, (1995) *Molecular Breeding,* 1(4):419-423 and Y. Yang et al. (2000) *The Plant Journal,* 22(6):543-551. A promoter that is "able to control transcription of operably linked nucleic acids in plants" refers to promoters that can direct transcription of an operably linked nucleic acid sequence in a plant cell. In an exemplary embodiment, "controlling transcription" refers to initiating transcription. In another exemplary embodiment, "controlling transcription" refers to up-regulating or down-regulating transcription compared to a basal constitutive level of transcription.

The term "operably linked" refers to a functional linkage between a nucleic acid expression control sequence (such as e.g., a promoter sequence, or array of transcription factor binding sites) and a second nucleic acid sequence, wherein the expression control sequence directs expression, e.g., transcription, of the nucleic acid corresponding to the second sequence. In an exemplary embodiment, a promoter that is "operably linked" to a heterologous nucleic acid is located upstream of and in-frame with the heterologous nucleic acid.

The term "heterologous" when used with reference to a nucleic acid, e.g., an MSD1 nucleic acid indicates that the nucleic acid is found in an environment that is not the same as found in nature (not naturally occurring). For instance, the nucleic acid may be recombinantly produced, or may be introduced, by methods known in the art, e.g., by transformation, genome editing or by introgression using marker assisted selection, into a different genetic background. In some exemplary embodiments, a heterologous nucleic acid has two or more sequences from unrelated sources arranged to make a new functional nucleic acid, e.g., a promoter from one source operably linked to a coding region from another source. Similarly, a heterologous protein indicates that the protein comprises two or more subsequences that are not found in the same relationship to each other in nature (e.g, a fusion protein). In some exemplary embodiments, the expression "heterologous nucleic acid sequence" or "heterologous gene" is used herein. The expressions refer to a gene that is not in its natural environment (in other words, has been altered by the hand of man an exemplary embodiment, a heterologous gene is a gene from one species that is introduced into another species, e.g., an MSD1 nucleic acid from *sorghum* introduced into a rice plant. In another exemplary embodiment, a "heterologous gene" or a "heterologous nucleic acid sequence" is a nucleic acid sequence joined to a regulatory element(s), e.g., a promoter that is not found naturally associated with the "heterologous gene" or "heterologous nucleic acid sequence".

An "expression cassette" as used herein, refers to a nucleic acid construct, typically generated recombinantly or synthetically, which comprises a series of specified nucleic acid elements that permit transcription of a particular nucleic acid in a host cell. In an exemplary embodiment, an expression cassette comprises a heterologous nucleic acid to be transcribed, operably linked to a promoter.

Typically, an "expression cassette" is part of an "expression vector". The term "vector" as used herein, refers to nucleic acid capable of replicating in a selected host cell or organism. A vector can replicate as an autonomous structure, or alternatively can integrate into the host cell chromosomes and thus replicate along with the host cell genome. Thus, an "expression vector" is a nucleic acid capable of replicating in a selected host cell or organism, e.g., a plasmid, virus, artificial chromosome, nucleic acid fragment, or any suitable construct known in the art, which comprises an "expression cassette".

The expression "enhanced grain yield" as used herein refers to an increase in grain yield from a grain crop plant that expresses an MSD1 nucleic acid as compared to the grain yield from a control grain crop plant that does not express an MSD1 nucleic acid. In an exemplary embodiment, the in crop plant that expresses an MSD1 nucleic acid is a *sorghum* plant that expresses an MSD1 nucleic acid and the control plant is an isogenic *sorghum* plant that does not express an MSD1 nucleic acid. In another exemplary embodiment, the grain crop plant that expresses an MSD1 nucleic acid is a rice plant that expresses an MSD1 nucleic acid and the control plant is an isogenic !ice plant that does not express an MSD1 nucleic acid. In another exemplary embodiment, the grain crop plant that expresses an MSD1 nucleic acid is a barley plant that expresses an MSD1 nucleic acid and the control plant is an isogenic barley plant that does not express an MSD1 nucleic acid. In another exemplary embodiment, the grain crop plant that expresses an MSD1 nucleic acid is a maize plant that expresses an MSD1 nucleic acid and the control plant is an isogenic maize plant that does not express an MSD1 nucleic acid. In another exemplary embodiment, the grain crop plant that expresses an MSD1 nucleic acid is a wheat plant that expresses an MSD1 nucleic acid and the control plant is an isogenic wheat plant that does not express an MSD1 nucleic acid.

Typically, grain yield is measured by bushels per acre or kg per hectare. Typically, grain yield is influenced by the number of plants per acre, seed number per plant, and seed weight. Among all these yield components, seed number per plant is a major determinant of grain yield in grain crops. Thus, grain yield is enhanced when seed number is increased. Therefore, increased seed number typically results in "enhanced grain yield". Accordingly, a "grain crop plant having enhanced grain yield" typically produces increased seed number with respect to a control in crop plant, e.g., a grain crop plant that expresses an MSD1 nucleic acid produces increased seed number as compared to an isogenic grain crop plant that does not express an MSD1 nucleic acid.

The term "transgenic plant" as used herein refers to a plant comprising a heterologous nucleic acid sequence that codes for or otherwise influences expression of the desirable trait of multi-seeded phenotype wherein the heterologous nucleic acid sequence was introduced into the plant, at some point in its lineage, by genetic engineering techniques, e.g., by genomic editing. Thus, the term "transgenic plant" refers to in crop plant which is the direct result of transformation with a heterologous nucleic acid or transgene, and the progeny and descendants of transformed plants which comprise the introduced heterologous nucleic acid or transgene.

A "non-transgenic plant" or as used herein, refers to a plant that does not comprise heterologous nucleic acid sequences for the desirable trait, either as a direct result of transformation with a heterologous nucleic acid or transgene, or as a result of inheritance as the progeny and descendants of transformed plants which comprise the introduced heterologous nucleic acid or transgene. Typically, the desirable traits of a "non-transgenic plant", e.g., increased seed number per plant, are produced and transmitted from one generation to the next by virtue of selective breeding techniques without the need for any genetic engineering techniques. Thus, a "non-transgenic plant" is a plant that is non-transgenic for genes and/or at loci that code for or otherwise influence the desirable trait.

"Induced mutation" or "induced variation" as used herein, refers to a change in a nucleic acid induced by physical or chemical agents that act on DNA thereby causing stable substitution of the nucleic acid present in the natural gene with a different nucleic acid. In an exemplary embodiment, "induced mutations" are transition mutations induced by mutagenesis with ethyl methane sulfonate (EMS).

Thus, the term "induced mutant" refers to a plant, e.g., a grain crop plant, carrying an induced mutation. In some exemplary embodiments, the induced mutant has phenotypic alterations that result from expression of the induced mutation in the "induced mutant", e.g., an induced mutation that, when expressed, results in a multi-seeded phenotype.

The term "transformation" as used herein encompasses any and all techniques by which a nucleic acid molecule might be introduced into a cell, including but not limited to, transfection with viral vectors, transformation with plasmid vectors, and introduction of naked DNA by electroporation, lipofection, Agrobacterium infection, and particle gun acceleration.

I. Introduction

The Poaceae (also called Gramineae or true grasses) are a large family of monocotyledonous flowering plants. With more than 10,000 domesticated and wild species, the Poaceae represent the fifth-largest plant family, and include important grain crops. The grain produced by members of the Poaceae plant family directly provides food for humans and as forage for domesticated animals, provides an indirect human food source as well. Exemplary grain crops that are members of the Poaceae family include e.g., wheat (*Triticum aestivum*), rice (*Oryza sativa*), corn/maize (*Zea mays*), *Sorghum bicolor*, barley, millet, etc.

Domestication of Poaceous cereal crops such as *sorghum*, maize, wheat, rice, barley, millet, etc., lies at the foundation civilization around the world, and the Poaceae still constitute the most economically important plant family in modern times. Accordingly, as discussed above, there is continual demand for increased productivity of grain crops as consumption for food, feed, and fuel continues to increase with increasing human population.

To meet increasing demand, now and into the future, new means for increasing productivity need to be developed. Fortunately, by providing grain crops with enhanced yield, the following disclosure provides just such means as are needed to meet worldwide demand for grain.

II. Grain Plants having Enhanced Yield.

A. General Methods

Methods disclosed herein utilize routine techniques in the field of genetics and cytogenetics. Basic terminology in the field of genetics and cytogenetics can be found in e.g., Robert C. King, William D. Stansfield, *A Dictionary of Genetics*, 6$^{th}$ ed., 2002, Oxford University Press. Techniques and methods for the cytological manipulation and analysis are well known to of skill in the art. See, e.g., Sybenga J., *Cytogenetics in Plant Breeding, Monographs on Theoretical and Applied Genetics*, vol. 17, 1992, Springer-Verlag, Berlin; Sharma A. K., Sharma A., Chromosome Techniques. Theory and Practice, 3$^{rd}$ ed., 1980, Butterworths, London; and Smith, C. W., Frederiksen, R., *Sorghum: Origin, History, Technology and Production*, 2000, John Wiley &. Sons, Inc., New York.

This disclosure also utilizes routine techniques in the field of recombinant genetics. Basic texts disclosing the general methods of use in this invention include Sambrook, et al., *Molecular Cloning—A Laboratory Manual*. 4$^{th}$ ed., 2012, Cold Spring Harbor Laboratory, Cold Spring Harbor, N.Y.; Kriegler, *Gene Transfer and Expression: A Laboratory Manual* 1990; and Ausubel, et al. (eds.), *Current Protocols in Molecular Biology*, 1994. Unless otherwise noted, technical terms are used according to conventional usage. Definitions of common terms in molecular biology maybe found in e,g., Benjamin Lewin, *Genes IX,* 2014, Oxford University Press; and Kendrew, et al. (eds.), *The Encyclopedia of Molecular Biology,* 1994, Blackwell Science Ltd.

For nucleic acids, sizes are given in either kilobases (kb) or base pairs (bp). Estimates are typically derived from agarose or acrylamide gel electrophoresis, from sequenced nucleic acids, or from published DNA sequences. For proteins, sizes are given in kilodaltons (kDa) or amino acid residue numbers. Proteins sizes are estimated from gel electrophoresis, from sequenced proteins, from derived amino acid sequences, or from published protein sequences.

Oligonucleotides that are not commercially available can be chemically synthesized, e.g., according to the solid phase phosphoramidite triester method first described by Beaucage & Caruthers, *Tetrahedron Letts.* 22:1859-1862 (1981), or using an automated synthesizer, as described in Van Devanter, et al.*Nucleic Acids Res.* 12:6159-6168 (1984). Purification of oligonucleotides is by either native acrylamide gel electrophoresis or by anion-exchange HPLC as described in Pearson & Reanier. *J. Chrom.* 255:137-149 (1983), The sequence of the cloned genes and synthetic oligonucleotides can be verified after cloning using, e.g., the chain termination method for sequencing double-stranded templates of Wallace et al., *Gene* 16:21-26 (1981).

B. Flower Structure and Seed Production of Poaceae (Gramineae)—the Grass Family

Flowers of Poaceae are characteristically arranged in spikelets, with each spikelet having one or more florets. The spikelets are grouped into panicles or spikes on which the seeds (grain) develop. Seed number per panicle is determined by several attributes of the inflorescence, including the number, and length, of the primary and secondary flower branches, and fertility of spikelets.

Typically, the spikelets consist of one sessile fertile spikelet and two lateral sterile pedicellate spikelets. Below the terminal spikelets, one or more spikelet pair can develop, and these adjacent spikelet pairs also consist of one sessile and one pedicellate spikelet.

Typically, in wild type plants, only the sessile spikelets develop into seeds. Indeed, in the course of normal development, the development of pedicellate spikelets is arrested at various stages. However, in exemplary embodiments, the mutant nucleic acid sequences disclosed herein are used to modify the genome of plants in the Poaceae family such that the development of pedicellate spikelets is no longer arrested and the pedicellate spikelets as well as the sessile spikelets are induced to produce seed. Seed number is thereby increased, and seed number is a major contributor to overall grain yield.

C. Sorghum and Induced Mutant *Sorghum* Plants

Wild type *sorghum* lines produce a main inflorescence, primary branches, secondary, and tertiary branches, which all end with a terminal spike consisting of one sessile complete spikelet (fertile floret) and two sterile pedicellate spikelets (florets with a pedicel). One or more adjacent (or non-terminal) spikes may also develop below the terminal spike. These adjacent spikes typically consist of one sessile and one pedicellate spikelet. Typically, for wild-type *sorghum*, only the sessile spikelets of terminal or adjacent spikes are complete flowers that will develop into mature seeds; the pedicellate spikelets are sterile and do not produce mature seed. These pedicellate spikelets are composed of bracts that do not develop reproductive organs and become chaffy structures.

In *sorghum* plants that exhibit a multi-seeded phenotype (msd), the pedicellate spikelets of the plant produce mature viable seed. Indeed, pedicellate spikelets exhibit complete flowers with full development of reproductive organs— functional gynoecium (ovary, style and stigma) and androecium (complete set of 3 anthers with copious amount of pollen). Therefore, seed yields per panicle in *sorghum* plants exhibiting the multi-seeded phenotype are greatly increased in comparison to wild-type *sorghum*, both in number of seeds produced and total seed weight per panicle or plant.

General techniques for the production of *sorghum* hybrids are well-known in the art (see e.g., U.S. Pat. No. 8,212,126).

D. Nucleic Acids Conferring the Multi-Seeded (msd) Phenotype

Mutant nucleic acids were isolated from a novel class of *sorghum* mutants characterized by increased number and length of the primary inflorescence branches, and production of fertile sessile and pedicellate spikelets. The isolated *sorghum* mutants were designated as multi-seeded (msd). The isolated *sorghum* mutants all bore mutations in the gene having accession number Sb07g021140 which is referred to herein as the MSD1 gene. Plants carrying an induced mutation in the MSD1 gene produce up to three times the seed number and twice the seed weight per panicle as compared to the wild type parent plant. Characterization of the mutants as disclosed herein below and in Example 2, reveals that particular mutations in the MSD1 gene are responsible for release of the suppression of the development of pedicellate spikelets and increased flower branch number and size. Accordingly, plants expressing MSD1 mutant nucleic acids provide for enhanced grain yield in these plants.

Orthologs of the Sb07g021140 gene are present in other cereal/grain crops such as, e.g., in maize, rice, barley, *Brachypodium*. Therefore, replacement of the orthologous genes with nucleic acids having an msd mutation as disclosed herein provides for other cereal plants that have increased seed numbers and hence enhanced grain yield per plant.

The coding sequence (cDNA) of the wild type of the *sorghum* gene having accession number Sb07g021140 (MSD1) is in SEQ If) NO: 1. The amino acid sequence of MSD1 wild-type protein is in SEQ ID NO: 29. Amino acids 80 to 138 of SEQ ID NO: 29 are a TCP domain. Mutants of this sequence as enumerated below and set forth in FIG. 2, confer the multi-seeded (msd) phenotype on plants expressing the sequence.

Mutant p23 (msd1-7)

The coding sequence (cDNA) of mutant p23 (msd1-7) has a mutation of G→A at position 230 of the MSD1 sequence. The cDNA sequence of mutant p23 is in SEQ ID NO: 2. The amino acid sequence of the mutant p23 MSD1 protein is in SEQ ID NO: 30. The G→A mutation in p23 changes the resulting protein sequence such that the arginine (R) amino acid at position 77 is changed to a glutamine (Q). Accordingly, other nucleic acid mutations that result in the same amino acid change will also confer the multi-seeded (msd) phenotype on plants expressing the sequences. Therefore, these nucleic acid sequences are also p23 MSD1 nucleic acids.

Mutant p10 (msd1-5)

The coding sequence (cDNA) of mutant p10 (msd1-5) has a mutation of G→A at position 244 of the MSD1 sequence. The cDNA sequence of mutant p10 sequence is in SEQ ID NO: 3. The amino acid sequence of mutant p10 MSD1 protein is in SEQ ID NO: 31. The G→A mutation in p10 changes the resulting protein sequence such that the aspartic acid (D) amino acid at position 82 is changed to an asparagine (N). Accordingly, other nucleic acid mutations that result in the same amino acid change will also confer the multi-seeded (msd) phenotype on plants expressing the sequences. Therefore, these nucleic acid sequences are also p10 MSD1 nucleic acids.

Mutant p15 (msd1-2)

The coding sequence (cDNA) of mutant p15 (msd1-2) has a mutation of C→T at position 289 of the MSD1 sequence. The cDNA sequence of mutant p15 is in SEQ ID NO 4. The amino acid sequence of the mutant p15 MSD1 protein is in SEQ ID NO: 32. The C→T mutation in p15 changes the resulting protein sequence such that the arginine (R) amino acid at position 97 is changed to a tryptophan (W). Accordingly, other nucleic acid mutations that result in the same amino acid change will also confer the multi-seeded (msd) phenotype on plants expressing the sequences. Therefore these nucleic acid sequences are also p15 MSD1 nucleic acids.

Mutant p12 (msd1-1)

The coding sequence (cDNA) of mutant p12 (msd1-1) has a mutation of at position 290 of the MSD1 sequence. The cDNA sequence of mutant p12 is in SEQ ID NO: 5. The amino acid sequence of the mutant p12 MSD1 protein is in SEQ ID NO: 33. The G→A mutation in p12 changes the resulting protein sequence such that the arginine (R) amino acid at position 97 is changed to glutamine (Q). Accordingly, other nucleic acid mutations that result in the same amino acid change will also confer the multi-seeded (msd) phenotype on plants expressing the sequences. Therefore, these nucleic acid sequences are also p12 MSD1 nucleic acids.

Mutant p18 (msd1-3)

The coding sequence (cDNA) of mutant p18 (msd1-3) has a mutation of position 368 of the MSD1 sequence. The cDNA sequence of mutant p18 is in SEQ ID NO: 6. The amino acid sequence of the mutant p18 MSD1 protein is in SEQ ID NO: 34. The C→T mutation in p18 changes the resulting protein sequence such that the threonine (T) amino acid at position 123 is changed to methionine (M). Accordingly, other nucleic acid mutations that result in the same amino acid change will also confer the multi-seeded (msd) phenotype on plants expressing the sequences. Therefore these nucleic acid sequences are also p18 MSD1 nucleic acids.

Mutant p2 (msd1-4)

The coding sequence (cDNA) of mutant p2 (msd1-4) has a mutation of C→T at position 382 of the MSD1 sequence. The cDNA sequence of mutant p2 is in SEQ ID NO: 7. The amino acid sequence of the mutant p2 MSD1 protein is in SEQ ID NO: 35. The mutation in p2 changes the resulting protein sequence such that the leucine (L) amino acid at position 128 is changed to phenylalanine (F). Accordingly, other nucleic acid mutations that result in the same amino acid change will also confer the multi-seeded (msd) phenotype on plants expressing the sequences. Therefore these nucleic acid sequences are also p2 MSD1 nucleic acids.

Mutant p5 (msd1-6)

The coding sequence (cDNA) of mutant p5 (msd1-6) has a mutation of at position 639 of the MSD1 sequence. The cDNA sequence of mutant p5 is in SEQ ID NO: 8. The amino acid sequence of mutant p5 MSD1 protein is in SEQ ID NO: 36. The G→A mutation in p5 changes the resulting protein sequence such that the protein is truncated at amino acid position 213. Accordingly, other nucleic acid mutations that result in the same truncation will also confer the multi-seeded (msd) phenotype on plants expressing the sequences. Therefore these nucleic acid sequences are also p5 MSD1 nucleic acids.

Nucleic acids conferring the multi-seeded phenotype as disclosed herein can be obtained by any method known in the art. Thus, in one exemplary embodiment, nucleic acids conferring the multi-seeded phenotype are synthetically made. Methods for chemically synthesizing nucleic acids such as polymerase chain reaction (PCR) are known in the art. See, e.g., Bartlett, J. M. and Stirling, D. (eds.) *PCR Protocols.* 2003, Humana Press.

In other exemplary embodiments, nucleic acids conferring the multi-seeded phenotype are isolated using any of a variety of methods known to those of skill in the art which may be used for isolation of nucleic acids. For example nucleic acids conferring the multi-seeded phenotype can be isolated from genomic DNA fragments of a *sorghum* plant having the multi-seeded phenotype. Thus, in an exemplary embodiment, nucleic acids conferring the multi-seeded phenotype are cloned from genomic DNA libraries using labeled oligonucleotide probes.

Other methods known to those of skill in the art can also be used to isolate nucleic acids conferring the multi-seeded phenotype. See, e,g., Sambrook, et al. for a description of other techniques for the isolation of DNAs related to DNA molecules of known sequence.

E. Construction of Grain Crop Plants Having Enhanced Grain Yield

1. Genome Editing

In an exemplary embodiment, genome editing is used to prepare grain crop plants having a multi-seeded phenotype.

Genome editing is known in the art. See, e.g., Voytas, D. F., 2013. Plant genome engineering with sequence-specific nucleases. *Annu. Rev. Plant Biol.* 64, 327-350; Harrison, M. M.,et al., 2014. A CRISPR view of development. *Genes Dev.* 28, 1859-1872; and Nekrasov, V., et al., 2013. Targeted mutagenesis in the model plant *Nicotiana benthamiana* using Cas9 RNA-guided endonuclease. *Nat Biotechnol,* 31, 691-693.

In an exemplary embodiment, MSD1 homolog genes are identified in maize, rice, *Brachypodium distachyon*, barley, *Triticum urartu*, and millet (*Setaria italica*) See discussion infra regarding the conserved amino acids at the msd1 mutation sites. Recombinant DNA restriction enzymes can be engineered by fusing a nuclease, for example FokI, with a structure that binds to a site in the MSD1 homologs, as specified by zinc finger, TALEN (Transcription activator-like effector nuclease), or CRISR (clustered regularly interspaced short palindromic repeat)-Cas9 system to make a double strand cut within the MSD1 homolog and replace with an engineered nucleic acids identified from the msd1 mutants. FokI is a bacterial type IIS restriction endonuclease consisting of an N-terminal DNA-binding domain, which can be made to bind specific DNA sequences in genome and a non-specific DNA cleavage domain at the C-terminal. Mutants in the MSD1 homolog can be selected from the crop for increasing grain number as disclosed herein.

2. Plant Transformation

In other exemplary embodiments, DNA constructs comprising an MSD1 nucleic acid operably linked to a promoter sequence can be used to transform grain crop plant cells and produce transgenic plants with desired phenotypic characteristics.

Exemplary plants for transformation with expression constructs comprising an MSD1 nucleic acid sequences include, but are not limited to; rice, barley, maize, *sorghum*, wheat, etc.

Transformation and regeneration of monocotyledonous and dicotyledonous plant cells is well known in the art. See, e.g., Weising, et al., *Ann. Rev. Genet.* 22:421-477 (1988); U.S. Pat. No. 5,679,558; Kevan M. A, Gartland, ed., *Agrobacterium Protocols*, 1995, Humana Press Inc.; and Wang, M., et al. *Acta Hort.* (ISHS) 461:401-408 (1998). The choice of method varies with the type of plant to be transformed, the particular application and/or the desired result. The appropriate transformation technique is readily chosen by the skilled practitioner.

Exemplary transformation/transfection methods available to those skilled in the art include, but are not limited to: direct uptake of foreign DNA constructs see e.g., EP 295959); techniques of electroporation (see, e.g., Fromm, et al., *Nature* 319:791 (1986)) high-velocity ballistic bombardment with metal particles coated with the nucleic acid constructs (see, e.g., Kline, et al., *Nature* 327:70 (1987), and U.S. Pat. No. 4,945,050); methods to transform foreign genes into commercially important crops, such as rapeseed (see De Block, et al., *Plant Physiol.* 91:694 701 (1989)), sunflower (Everett, et al., *Bio/Technology* 5:1201 (1987)), soybean (McCabe, et al., *Bio/Technology* 6:923 (1988); Hinchee, et al., *Bio/Technology* 6:915 (1988); Chee, et al., *Plant Physiol.* 91:1212-1218 (1989); Christou, et al., *Proc. Natl. Acad. Sci. USA* 86:7500-7504 (1989); EP 301749), rice (Hiei, et al., *Plant J.* 6:271-282 (1994)), corn (Gordon-Kamm, et al., *Plant Cell* 2:603-618 (1990); Fromm, et al., *Biotechnology* 8:833-839 (1990)), and Hevea (Yeang, et al., In, *Engineering Crop Plants for Industrial End Uses*, Shewry, et al, (eds.), Portland: London, 1998; pp 55-64). Other known methods are disclosed in, e.g., U.S. Pat. Nos. 5,597,945; 5,589615; 5,750,871; 5,268,526; 5,262,316; and 5,569,831.

Another exemplary method includes: transformation with DNA employing *Agrobacterium tumefaciens* or *Agrobacterium rhizogenes* as the transforming agent, electroporation, particle acceleration, etc. (e.g., EP 295959 and EP 138341). In one exemplary embodiment, Ti-derived vectors are used to transform a wide variety of higher plants, including dicotyledonous plants, such as, e.g., potato, soybean, cotton, rape, tobacco, and rice. See, e.g., Pacciotli et al., *Bio/Technology* 3:241 (1985); Byrne, et al., *Plant Cell, Tissue and Organ Culture* 8:3 (1987); Sukhapinda, et al., *Plant Mol. Biol.* 8:209-216 (1987); Lorz, et al., *Mol. Gen. Genet.* 199:178 (1985); Potrykus, (1985) supra; Park, et al., *J. Plant Biol.* 38(4):365-71 (1995); and Hiei, et al., *Plant J.* 6:271-282 (1994).

*Agrobacterium tumefaciens*—meditated transformation techniques are well described in the scientific literature. See, e.g., Horsch, et al. *Science* 233:496-498 (1984), and Fraley, et al. *Proc. Natl. Acad. Sci. USA* 80:4803 (1983). Typically, a plant cell, an explant, a meristem or a seed is infected with *Agrobacterium tumefaciens* transformed with the expression vector/construct which comprises MSD1 nucleic acid. Under appropriate conditions known in the art, the transformed plant cells are grown to form shoots, roots, and develop further into plants. The nucleic acid segments can be introduced into appropriate plant cells, for example, by means of the Ti plasmid of *Agrobacterium tumefaciens*. The Ti plasmid is transmitted to plant cells upon infection by *Agrobacterium tumefaciens*, and is stably integrated into the plant genome (Horsch, et al., *Science*, 233:496-498 (1984); Fraley, et al., *Proc. Nat'l. Acad Sci. USA* 80:4803 (1983).

Transformed plant cells which are derived by any of the above transformation techniques can be cultured to regenerate a whole plant which possesses the desired transformed phenotype. Such regeneration techniques rely on manipulation of certain phytohormones in a tissue culture growth medium, typically relying on a biocide and/or herbicide marker which has been introduced together with the desired nucleotide sequences. Plant regeneration from cultured protoplasts is described in Evans, et al., *Protoplasts Isolation and Culture, Handbook of Plant Cell Culture*, pp. 124-176, MacMillan Publishing Company, New York, 1983; and Binding, *Regeneration of Plants, Plant Protoplasts*, pp. 21-73, CRC Press, Boca Raton, 1985, all of which are incorporated herein by reference. Regeneration can also be obtained from plant callus, explants, organs, or parts thereof. Such regeneration techniques are described generally in Klee, et al. *Ann. Rev. of Plant Phys.* 38:467-486 (1987).

One of skill will recognize that, after an expression cassette comprising an MSD1 nucleic acid is stably incorporated in transgenic plants and confirmed to be operable, it can be introduced into other plants by sexual crossing. Any of a number of standard breeding techniques can be used, depending upon the species to be crossed.

3. Marker Assisted Rapid Trait Introgression (MARTI)

Marker-assisted selection (MAS) is a method of selecting desirable individuals in a breeding scheme based on DNA molecular marker patterns instead of, or in addition to, their phenotypic traits. MAS provides a useful tool that allows for efficient selection of desirable crop traits and is well known in the art. See, e.g., Podlich, D. W., et al., *Crop Sci.* 44:1560-1571 (2004); Ribaut, J. M., and D. Hoisington, *Trends in Plant Sci.* 3:236-238 (1998); Knapp, S., *Crop Sci.* 38:1164-1174 (1998); and Hospital, F., *Marker-assisted breeding*, pp. 30-59, in H. J. Newbury (ed.) *Plant molecular breeding*, 2003, Blackwell Publishing and CRC Press, Oxford and Boca Raton.

As is well known in the art, breeders typically improve crops by crossing plants with desired traits, such as high yield or disease resistance, and selecting the best offspring over multiple generations of testing. Thus, new varieties can easily take 8 to 10 years to develop. In contrast to conventional selection methods, with marker-assisted selection plants are selected based on molecular marker patterns known to be associated with the traits of interest. Thus, marker-assisted selection involves selecting individuals based on their marker pattern (genotype) rather than their observable traits (phenotype). Thus, molecular marker technology offers the possibility to speed up the selection process and thus offers the potential to develop new cultivars quickly.

Therefore, in an exemplary embodiment, MAS is used to develop new *sorghum* cultivars having the multi-seeded phenotype. In this embodiment, the single nucleotide polymorphisms disclosed herein are used as markers to select for the multi-seeded phenotype.

In general, the basic procedure for conducting MAS with DNA markers is as follows: 1. Extracting DNA from tissue of each individual or family in a population. 2. Screening DNA samples via PCR for the molecular marker (SSR, SNP, SCAR, etc.) linked to the trait of interest. 3. Separating and score PCR products, using an appropriate separation and detection technique. 4. Identifying individuals exhibiting the desired marker allele. 5. Combining the marker results with other selection criteria (e.g., phenotypic data or other marker results), select the best fraction of the population, and advance those individuals in the breeding program.

III. Measuring Grain Yield

Grain yield is usually measured by bushels per acre or kg per hectare. Grain yield is typically influenced by the number of plants per acre, seed number per plant, and seed weight. Among all these yield components, seed number per plant is a major determinant of grain yield in grain crops. Indeed, grain yield of the exemplary grain crop, sorghum [*Sorghum bicolor* (L.) Moech] and other cereal/grain crops (see e.g. Saeed, et' al., *Crop Sci.* 26:346-351 (1986); Duggan, et al., *Can. J. Plant Sci.* 80:739-745 (2000); Richards, *J. Exp. Bot.* 51:447-458 (2000); Ashikari, et al., *Science* 309:741-745 (200:5); Reynolds, et al., *J. Exp. Bot.* 60:1899-1918 (2009)) is greatly influenced by the number of seeds per plant. Thus, increased seed number and seed size, which is directly related to improved grain yield, is a common goal during domestication of cereal crops. Over time, this has resulted in inadvertent selection of genetic stocks with greater seed number and larger seeds (see, e.g., Zohary, et al., *Domestication of Plants in the Old World: The Origin and Spread of Cultivated Plants in West Asia, Europe, and the Mediterranean Basin* 4$^{th}$ ed., 2012 Oxford University Press, Oxford, U.K.

The following examples are offered to illustrate, but not to limit the invention.

EXAMPLES

Example 1

The following example illustrates identification of nucleic acid sequences that, when expressed in a grain crop plant, e.g., a *sorghum* plant, confers a multi-seeded phenotype on the grain crop plant. Nucleic acid sequences were identified using next-generation sequencing of pooled genomic DNA of homozygous msd1 mutants selected from a backcrossed $F_2$ population. Confirmation of the identity of the gene was achieved by sequencing other independent alleles of msd1-1. The trait can be bred into other *sorghum* lines by selection of the mutation in the gene.

Materials and Methods

Plant Materials and DNA Sequencing on Illumina HiSeq2000

Sorghum [*Sorghum bicolor* (L.) Moench] msd mutants were identified from a pedigreed *sorghum* mutant library that was created by mutagenizing BTx623 seeds with the chemical mutagen, ethyl methance sulfonate (EMS) (Xin, et al., *BMC Plant Biol.* 8:103 (2008)). The first confirmed mutant (p12, stands for putative msd mutant #12), re-named as msd1-1, was backcrossed to the wild type BTx623 in a greenhouse. The wild type BTx623, 17 independent msd mutants, and the backcrossed $F_2$ seeds of msd1-1 mutant were planted in the field of USDA-ARS Agricultural Experiment Station at Lubbock, Tex. (33'39" N, 101'49" W) on May 19, 2012. During late grain filling stage, 50 homozygous msd1-1 mutants observed from the backcrossed $F_2$ plants were selected. Leaf samples were collected from each of the homozygous mutants to prepare genomic DNA using a method described earlier (Xin and Chen, *Plant Methods* 8:26 (2012)). Equal amounts of genomic DNA was pooled from the 50 individual $F_2$ mutants and diluted to 100 ng/µl.

Gene Identification by Next-generation Sequencing

The pooled genomic DNA, and genomic DNA from BTx623, msd1-1, and 16 additional independent homozygous msd mutants were sequenced by illumina HiSeq2000 at Beijing Genomic Institutes (genomics.cn). The pooled genomic DNA for msd1-1 $F_2$ population was submitted as two samples. Genomic DNA from BTx623 and the individual msd mutants was submitted as one sample each (i.e., ⅓ of a sequencing lane). Low quality reads, adaptor sequences, and contamination were first excluded from the raw reads. Then the clean reads were aligned to the *sorghum* reference genome v1.4 with Bowtie2 (Langmead and Salzberg, *Nat Methods* 9:357-9 (2012)). The SNP calling was done by Samtools and Bcftools using only the reads with mapping and sequencing quality more than 20 (Li, et al., *Bioinformatics* 25:2078-9 (2009)). For the parental line BTx623 and individual msd mutants, the read depth for SNPs was set from 3 to 50, and from 5 to 100 for the msd1-1 $F_2$ population. The SNPs from BTx623 were treated as background noise and were filtered from all the mutants and $F_2$ population. Because EMS is known to induce only G/C to A/T transition mutations (Greene, et al., *Genetics* 164: 731-40 (2003)), only the homozygous and G/C to A/T SNPs from $F_2$ population and 17 mutants were processed to effect prediction by Ensembl variation predictor (McLaren, et al., *Bioinformatics* 26:2069-70 (2010)). The homology analysis and functional annotation of candidate genes were obtained from Gramene database release 39 (Monaco, et al., *Nucleic Acids Res.* 42:D1193-9 (2014)) (gramene.org). The coding DNA sequence (CDS) and protein translation of Sb07g021140 were obtained based on annotation from phytozome.net (©, 2006-2014 University of California, gramene.org). See, e.g., Monaco M K, et al. (2014) *Gramene* 2013: comparative plant genomics resources. *Nucleic Acids Res.* 42 (D1): D1193 -D1199. PMID: 24217918. doi : 10.1093/nar/gkt1110; Youens-Clark K, et al, (2011). *Gramene database in* 2010: *updates and extensions. Nucleic Acids Res.* 39: D1085-94. PMID: 21076153 doi: 10.1093/nar/gkq1148; Liang C, et al, (2008). *Gramme: a growing plant comparative genomics resource. Nucleic Acids Res.* 36 :D947-53, PMID: 17984077; Jaiswal P, et al, (2006). *Gramene: a bird's eye view of cereal genomes. Nucleic Acids Res.* 34: D717-723; Ware D, et al, (2002). *Gramme: a resource for comparative grass genomics. Nucleic Acids Res.* 30, 103-105; Ware D H, et al. (2002). *Gramme, a tool for grass genomics. Plant Physiology* 130: 1606-1613; and *Sorghum bicolor* assembly v1.4. The total CDS has 774 bases and encodes a protein with 257 amino acids.

Confirmation of the Causal SNPs with Sanger Sequencing

In addition to p12 (msd1-1), p15 (msd1-2), p18 (msd1-3), p2 (msd1-4), p5 (msd1-6), p23 (msd1-7), and p10 (msd1-5) also harbor mutations in Sb07g021140 based on the next generation sequencing data. These mutants and wild type BTx623 were utilized to confirm the transition mutations obtained from the next generation sequencing data. Briefly, the whole 774-nucleotide sequence of Sb07g021140 was amplified using specific forward and reverse primers (frodo.wi.mit.edu/primer3/input.htm). The target genomic DNA containing the mutation was amplified using Phusion high fidelity DNA polymerase (New England Biolabs) from each of the msd mutants and the wild type BTx623. All PCR products were purified with QIAquick PCR purification kit (Qiagen) before use as templates for sequencing. Subsequently, the nested sequencing primers that encompass predicted SNP were designed and used for fluorescent Sanger sequencing on ABI Genetic Analyzer 3130 XL (Life Technology, Grand Island, N.Y.). DNA sequences were assembled and analyzed with DNAMan software (Lynnon Corp.) at the chromatogram level to verify the mutations.

Co-segregation Analysis of msd Phenotype and the Causal SNP

To further confirm the causal SNPs thus identified, 20 individuals with known msd phenotype were genotyped for each of the appropriate msd1 allele using rapid genotyping method known as Kompetitive Allele Specific PCR (KASP) by design (KBioscienc/LGC Genomics [lgcgenomics.com]) based on manufacturer's protocols with some modifications.

Briefly, the touchdown PCR for msd primers used was 65° C. to 57° C. and actual PCR was performed for 30 cycles using an annealing temperature of 57° C. Rapid genotypic screening and co-segregation of the causal SNPs with the msd phenotype were further verified in three independent $F_2$, breeding populations involving cross of msd1-1 (p12 in BTx623 background) to RTx437, BTx642, and RTx430. Each population is represented by 48 individuals. Since msd trait was scored as binary trait, SNP-trait relationship was analyzed using Fisher's exact test.

Results and Discussion

Phenotype of the msd1 Mutants

From the pedigreed *sorghum* mutant library created at the Plant Stress and Germplasm Development Research Unit of USDA-ARS at Lubbock, Tex., a series of mutants were identified that have coordinated changes of increased number of flower branches, increased size of flower branches, and full fertility of pedicellate spikelets [(Xin, Z., et al., 2008. *BMC Plant Biology* 8, 103); Burow, G., et al., 2014. *Crop Science* 54, 2030-2037)]. These coordinated phenotypic changes lead to a potential three-fold increase in seed number and twice increase in seed weight per panicle. In all characterized natural *sorghum* lines, only the sessile spikelets are fertile. In this class of mutants, all spikelets, sessile and pedicellate, developed into perfect flowers and produced seeds. In all the msd mutants characterized, the coordinated phenotypic changes are due to recessive mutations on a single nuclear gene.

Thus, the causal gene mutations were identified through mutant mapping by next-generation-sequencing (Abe, A., et al., 2012. *Nature Biotechnology* 30, 174-178).

Identification of Candidate Genes from the Backcrossed Mapping Population and Independent Alleles To identify the causal gene mutations responsible for the msd mutant phenotype, the genomic DNA pooled from a backcrossed $F_2$ population of msd1-1 by BTx623 and individual parental line BTx623, msd1-1 (p12), and other msd mutants were sequenced on Illumina 2000 HiSeq2000. The sequencing generated ~27.1× coverage for the pooled $F_2$ population, ~12.9× coverage of BTx623, and an average of ~12× coverage for each individual msd mutant. Based on the genetic background, the homozygous SNPs from G/C to A/T transition were considered as candidate SNPs. Based on SNP calling and filtering pipeline, 14 homozygous candidate SNPs in the pooled msd1-1 (p12) $F_2$ population and 90 in the homozygous msd1-1 (p12) mutant were identified. Four genes with unique SNPs overlapped between pooled $F_2$ population and the individual p12 mutant. Mutant p12 (msd1-1) and p18 (msd1-3) were known to be allelic through previously genetic complementary test. Comparing the four candidate SNPs with that in p18 (msd1-3), only one gene, Sb07g021140, contains unique SNPs in each of the two mutants. The gene has a size of 1,141 bases (including UTR). The coding DNA sequence (CDS) has 774 bases (SEQ ID NO: 1) and encodes a protein with 257 amino acids (SEQ ID NO: 29). Amino acids from 80 to 138 in SEQ ID NO: 29 are the TCP domain. Five other msd mutants, p2 (msd1-4), p5 (msd1-6), p10 (msd1-5), p15 (msd1-2), and p23 (msd1-7) also harbor unique mutations in the gene.

Confirmation of the Putative SNPs by Sanger Sequencing

To verify the 7 unique mutations in the gene Sb07g021140 from the next generation sequencing data, the genomic DNA from all the msd1 alleles were re-sequenced by Sanger sequencing on ABI Genetic Analyzer 3130XL. Mutation in each of the mutants was confirmed by Sanger sequencing supporting the hypotheses that Sb07g021140 is likely the gene mediating the mutant msd phenotype. See discussion, supra and infra, regarding the SNPs.

Co-segregation of the SATs with the msd Phentotype

To further demonstrate Sb07g021140 is indeed the gene that mediates the msd phenotype, co-segregation of the DNA mutation with the msd phenotype was analyzed in a breeding $F_2$ population of RTx437 by p12 using KASP rapid genotyping method. Among 48 individual $F_2$ plants, 10 plants were scored as homozygous mutant SNPs, 11 as homozygous wild type SNPs, and 27 were heterozygous. All 10 $F_2$ plants with homozygous mutant SNP displayed msd1 panicles and the rest of $F_2$ plants displayed normal panicles (FIG. 1). Combining with genetic variation characterized by Sanger sequencing, the co-segregation analysis suggests, Sb07g021140 is the causal gene for the msd1 trait.

MSD1 Encodes a TCP Domain Transcription Factor

Figure 2:
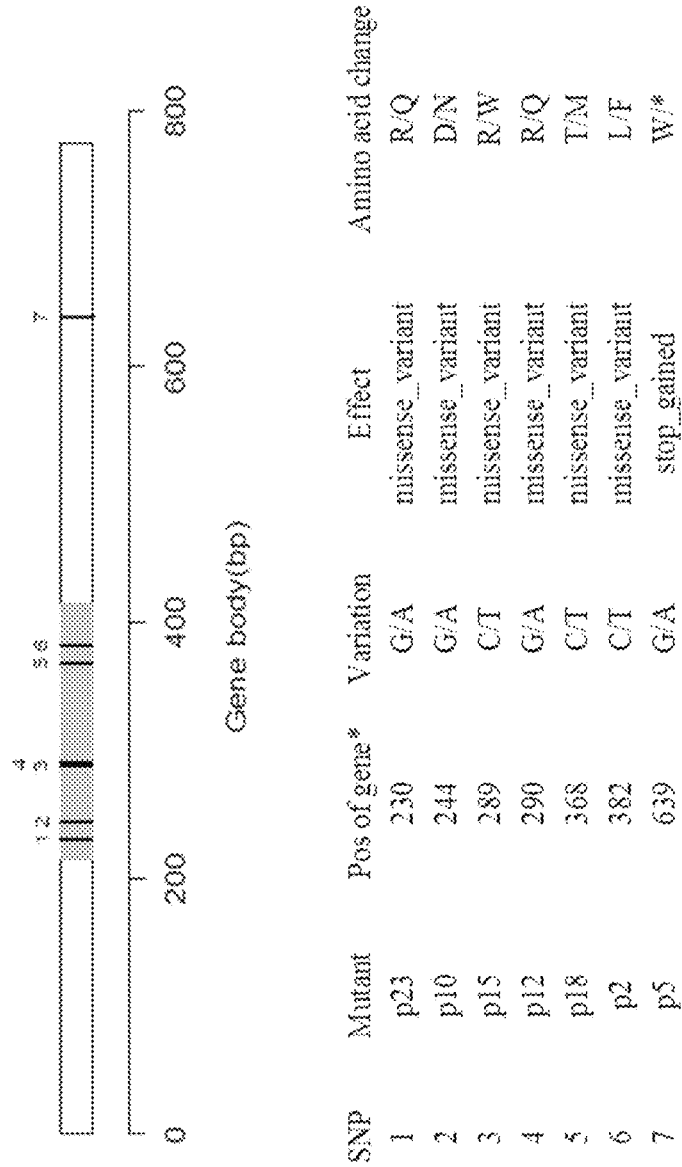
FIG. 2 shows MSD1 gene model and position of the causal SNPs. The shaded area is the TCP domain. The numbers above are the SNP position, which are given below the graph.

Sequencing analysis indicates that Sb07g021140 encodes a plant-specific transcription factor with a TCP domain; amino acids from 80 to 138 in SEQ ID NO: 29. The TCP domain is first described in 1999 as an amino acid motif found in Teosinte Branched 1 (TB1), Cycloidea (CYC), and Proliferating Cell nuclear binding Factor I and II (PCF1 and PCF2), four apparently unrelated plant transcription factors (Cubas, et al., *Plant J.* 18:215-22 (1999)). The TB1 gene encodes a transcription factor that suppresses basal tiller development and promotes femaleness for upper node tillers in maize (Doebley, et al., *Genetics* 141:333-46 (1995); Doebley, et al., *Nature* 386:485-8 (1997)). The CYC controls flower asymmetry in *Antirrhinum* by suppressing the initiation and reducing the growth rate of floral organs in the dorsal region of the wild-type meristem (Luo, et al., *Nature* 383:794-9 (1996)). The rice PCF1 and $PCF_2$ are transcription factors that binds to the promoter region of proliferating cell nuclear antigen that is induced during G1 to S phase transition during cell division (Kosugi and Ohashi, *Plant Cell* 9:1607-19 (1997)). FIG. 2 showed the gene model of MSD1 and positions of the causal SNPs (mutations) in the gene. 7 independent mutant alleles for MSD1 gene were isolated; all six nonsynonymous-SNPs are located in the TCP domain. One SNP (G639A) outside the TCP domain is a nonsense mutation that changed the codon TGG for tryptophan to a stop codon TAG. The distribution of the SNPs indicated that TCP domain play an important role in the function MSD1 protein.

MSD1 is a Member of Multi-gene Family with 24 Members in the *sorghum* Genome

TCP domain proteins are a family of plant-specific transcription factors that shape the plant form and architecture (Manassero, et al., *BioMolecular Concepts* 4 (2013)). To identify other members of TCP domain proteins in *sorghum*, a search was conducted using Biomart in Gramene with the TCP domain (pfam id: PF03634) (Monaco, et al., 2013). A total of 28 genes were identified—Sb014.7,026970; Sb06g023130; Sb04g038140; Sb06g002260; Sb03g019411; Sb06g016340; Sb03g019510; Sb03g013360; Sb03g044320; Sb08g021725; Sb04g027960; Sb10g008030; Sb02g030260; Sb08g004600; Sb08g004610; Sb05g004800; Sb08g019710; Sb02g024450; Sb07g021140; Sb03g001940; Sb03g034918; Sb09g025340; Sb03g035350; Sb02g003070; Sb02g013020; Sb01g006020; Sb08g021690; and Sb01g010690. Three of the genes (Sb03g019510; Sb08g004610; and Sb02g013020) have incomplete TCP domains, and one (Sb08g019710) has no typical TCP domain (conserved sequences). The remaining 24 genes were analyzed for phylogenetic relationship (FIG. 3) using Mega 5.2.2 (Tamura, et al., *Mol Biol Evol* 28:2731-9 (2011)). The MSD1 protein belongs to the CYC/

TB1 sub-group in the class II TCP domain proteins. CYC gene is originally isolated from *Antirrhinum* as a regulator of flower asymmetry (Luo, et al., 1996). In the wild type *Antirrhinum*, CYC is expressed at the dorsal (adaxial) side of the apical meristem during the stage of sepal primordia initiation to inhibit the initiation of sepal, petal, and stamen. Thus, the wild type flower has five sepals, five petals, four stamens, and one aborted stamen (called staminode) at the dorsal side. In the cyc mutants, the suppression of initiation and growth of flower organs is abolished. The staminode at the dorsal side becomes a fully developed stamen. In addition, a new stamen at the dorsal side is initiated and fully developed. Thus, the cyc flower has six sepals, six petals, and six stamens. The CYC also expressed at the dorsal side of the flower during late stage of flower development to affect the asymmetry of the *Antirrhinum* flower. Similar to the function of CYC in *Antirrhinum* in suppression of the initiation and development of flower organs in the dorsal side, the MSD1 may function as a suppressor to arrest the development of the pedicellate spikelets. Because the msd1 mutants also have increased number and size of the primary inflorescence branches, MSD1 may also inhibit the initiation of primary inflorescence branch primordia and arrest the growth the inflorescence branches at late stage of the panicle development.

TB1 is a gene identified in maize that controls the apical dominance by inhibiting the development of basal tillers (Doebley, et al., 1997). The tb1 mutants produce massive number of basal tillers. Its rice ortholog (OS03G49880 201) also functions as a suppressor of tiller development (Takeda, et al, *Plant J* 33:513-20 (2003)). The *sorghum* ortholog of TB1 is Sb01g010690. This gene has been shown to be induced by high planting density and far-red light enrichment, a condition that reduces tiller development (Kebrom, et al., *Plant Signal Behav* 5:317-9 (2010)). Thus, it is likely that the *sorghum* homolog of TB1 may also mediate tiller development. As a distinct clade from TB1, MSD1 may have evolved new functions in mediating panicle development and pedicellate spikelet fertility rather than tiller development.

Figure 3:
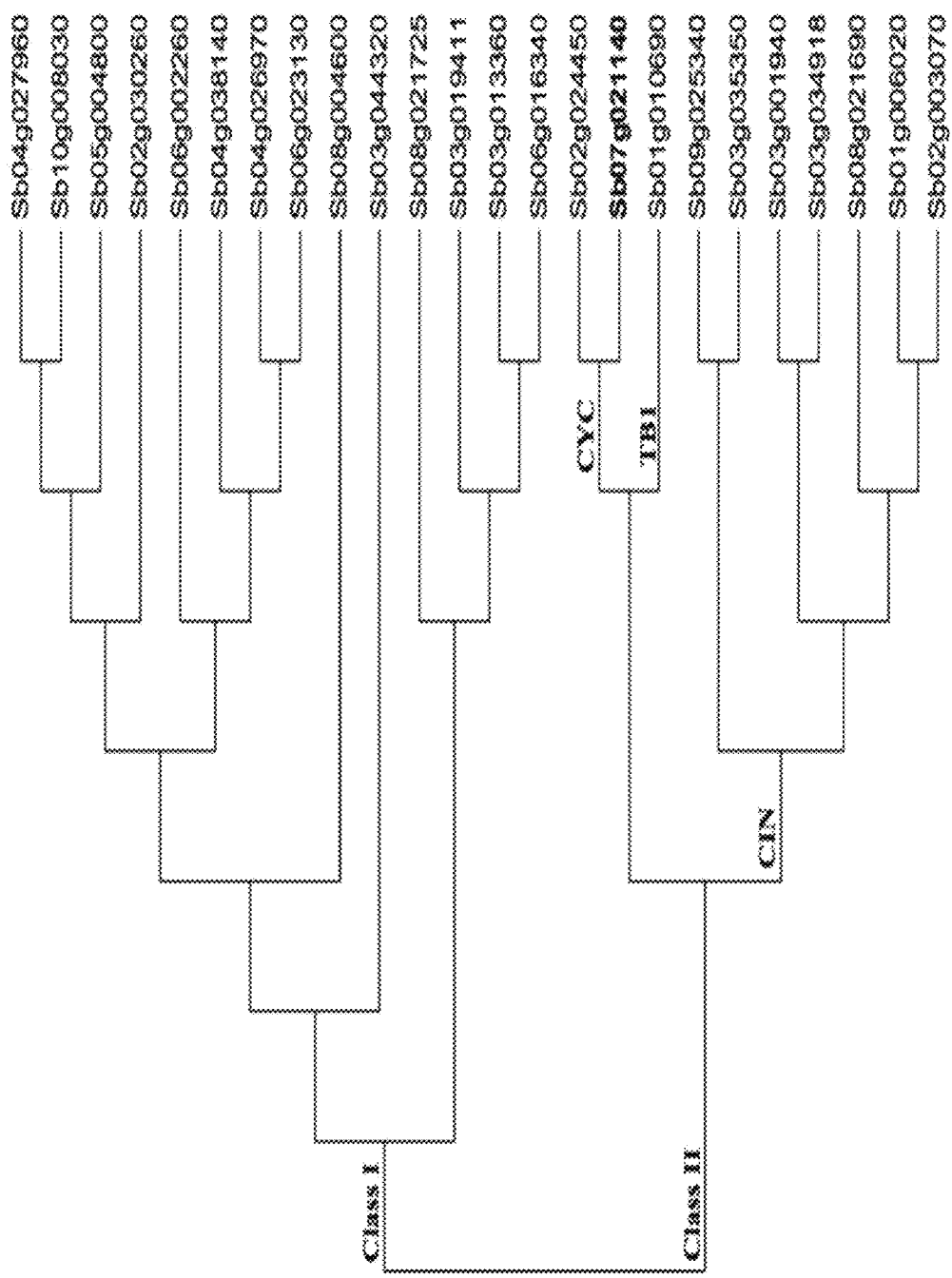
FIG. 3 illustrates the phylogenetic relationship of the twenty-four *sorghum* proteins identified having a TCP domain. After removing the four genes with an incomplete TCP domain, the phylogenetic relationship of the remaining 24 proteins were plotted. The MSD1 proteins belong to class II TCP proteins in the CYC/TB1 group.
Figure 4:
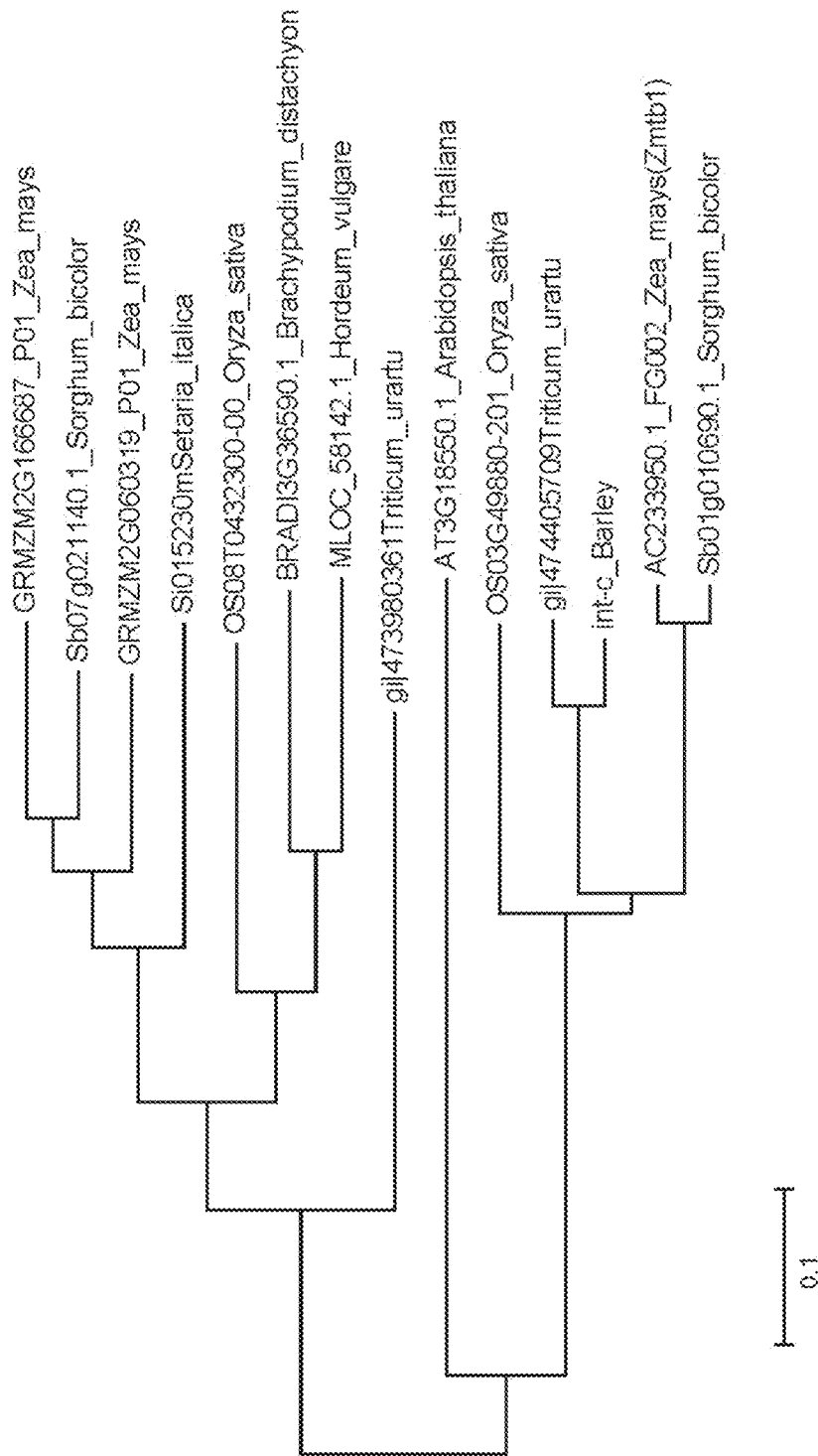
FIG. 4 illustrates the phylogenetic relationship of MSD1 and its orthologs to TB1. The phylogenetic relationship of MSD1 and its orthologs from other grass species were compared with TB1 and its orthologs.

MSD1 orthologs were found in maize (GRMZM2G166687_p01 and GRMZM2G060319_P01), rice (OSO8T0432300-00), barley (MLOC_58142.1), and other grass species (*Brachyodium distachyon*—BRADI3G36590.1; *Triticum Urartu*—gi|473980361; and *Setaria italica*—Si015230m), Five MSD1 orthologs, two from maize, one from rice, barley, and brachypodium, were identified through searching Gramene based on sequence similarity and syntenic positions on chromosome. The phylogenic analysis of all the *sorghum* TCP proteins indicated that MSD1 is closely related to TB1 but not the ortholog of TB1 (FIG. 3). When TB1 and its *sorghum* and *Arabidopsis* orthologs were included in the phylogenic analyses, the MSD1 and its orthologs were grouped into a different clade from the TB1 orthologs (FIG. 3, FIG. 4), indicating that the MSD1 gene and its orthologs have evolved novel functions that are distinct from TB1. When the MSD1 and its orthologous proteins from other plants are aligned, all the amino acids that have been mutated in msd1 mutant alleles are conserved in six proteins (not conserved at one amino acid in *Triticum Urartu*—gi|473980361), indicating that these amino acids are critical to the function of the MSD1 protein and probably its orthologs in other crops, as well. The MSD1 orthologs from other cereal crops may play a similar role to repress the development certain type of spikelets or florets.

Barley inflorescence has a very different architecture from *sorghum*. It has a single indeterminate main inflorescence axis that produces three single-flowered spikelets in a distichous manner at each rachis internode (Koppolu, et al., *Proc. Natl. Acad. Sci. USA* doi:10.1073/pnas.1221950110 (2013)). In the ancestral two-row barley, each central fertile spikelet is accompanied with two lateral aborted spikelets. In six-row barley, the two lateral spikelets are also fertile. There are at least five genetic loci that contribute to the conversion of two-row to six-row barley (Koppolu, et al., 2013). Three loci have been cloned. The VRS1 encodes a homeodomain-leucine zipper class I transcription factor that is a negative regulator of lateral spikelet fertility (Komatsuda, et al., *Proc. Natl. Acad. Sci. USA* 104:1424-1429 (2007)). The Intermedium-C (Int-C) locus in barley encodes TB1 homolog, which modifies the lateral spikelet development in certain vrs1 allele background (Ramsay, et al., *Nat. Genet.* 43:169-72 (2011)). The VRS4 is homolog of maize Ramosa 2, a gene controls inflorescence branching in maize (Bortiri, et al. The Plant Cell 18 (2006)). Among the three cloned barley genes, Int-C and MSD1 belong to the same CYC/TB1 class of the TCP domain proteins, although Int-C is more closely related to the *sorghum* TB1 ortholog Sb01g010690 than to MSD1. We sequenced the *sorghum* homolog of barley VRS1 from 17 independent msd mutants and found no mutation in the *sorghum* homolog (Burow, et al., 2014). The *sorghum* ortholog of VRS4 has not been sequenced from the *sorghum* msd mutants. From these results, it appears that the pathway that controls row number in barley and inflorescence branching and fertility of pedicellate spikelets in *sorghum* may overlap and may also recruit components specific in each species.

In maize, the flower inflorescence diverged into tassel (male inflorescence) and ear (female inflorescence) (Bommert, et al., *Plant Cell Physiol.* 46:69-78 (2005)). Both tassel and ear inflorescences consist of spikelet pairs and both spikelets are fertile. In the ear, each spikelet in the spikel et pairs has two florets, only the upper floret can develop into a seed; the lower floret will eventually abort (Bommert, et al., 2005). *Sorghum* diverged from maize about 11 million year ago (Paterson, et al., *Proc. Natl. Acad. Sci. USA* 101:9903-8 (2004). The two maize ortholog,s of MSD1, which belong to a different dale from TB1, may control similar processes as a suppressor of the development of certain type of florets.

Rice shares a common ancestor with *sorghum* about 20 million years ago (Paterson, et al., 2004). Similar with *sorghum*, rice also has highly branched panicles with bisexual flowers. However, rice panicles bear only mono spikelet with a single floret at each flower node, instead of spikelet pairs (Ikeda, et al., *Breeding Science* 54:147-156 (2004)). Each fertile spikelet is subtended with a pair of empty glumes (also called sterile lemma), and a pair of rudimentary glumes. Recent evidence shows that the empty glumes, which are much larger than the rudimentary glumes, may be derived from the lemmas of two sterile spikelets that have been reduced during the evolution of rice (Yoshida, et al., *Proc. Nat. Acad. Sci. USA* 106:20103-20108. doi: 10.1073/pnas.0907896106 (2009); Jin, et al., *Dev. Biol.* 359:277-88 (2011)). Like CYC in *Antirrhinum* and MSD1 in *sorghum*, the rice MSD1 ortholog may also play a role in suppression of the development of the empty glumes.

The msd mutants define a novel coordinated phenotype, increased number and size of flower branches and full fertility of both sessile and pedicellate spikelets, in *sorghum*. No natural *sorghum* accession has been reported to display this coordinated phenotype. To determine if this gene has any polymorphism among *sorghum* lines or this gene has been subjected to breeders' selection, we searched the gene sequence from 44 whole genome-sequenced *sorghum* accessions (Mace, et al., *Nature Communications* 4:2320 (2013)) and SAP population SNPs (a total of 378 lines) that has been sequenced partially by genotype by sequencing (Mace, et al., 2013; Morris, et al., *Proc. Natl. Acad. Sci. USA* 110: 453-8 (2013)). No polymorphism, or evidence of selection, was found in this gene. Thus, increasing seed number in *sorghum* through mutation in MSD1 gene is a novel process enabled by the mutation analysis and identification of the gene.

Example 2

The following example illustrates the use of genome editing to incorporate MSD1 mutations into grain crops. This is a prophetic example.

Targeted genome engineering (also known as genome editing) is useful for introducing mutations in specific DNA sequences. See, e.g., Belhaj, K., et al., *Plant Methods* 9, 39 (2013); Jiang, W., et al., *Nucleic Acids Res*, 41, e188 (2013)). The CRISPR/Cas system for genome editing is based on transient expression of Cas9 nuclease and an engineered single guide RNA (sgRNA) that specifies the targeted nucleic acid sequence.

Cas9 is a large monomeric DNA nuclease guided to a DNA target sequence with the aid of a complex of two 20-nucleotide (nt) non-coding RNAs: CRIPSR RNA (crRNA) and trans-activating crRNA (tracrRNA), which are functionally available as single synthetic RNA chimera. The Cas9 protein contains two nuclease domains homologous to RuvC and HNH nucleases. The HNH nuclease domain cleaves the complementary DNA strand whereas the RuvC-like domain cleaves the non-complementary strand and, as a result, a blunt cut is introduced in the target DNA.

When the Cas9 and the sgRNA are transiently expressed in living cells, double strand breaks (DSBs) in specific targeted genomic DNA is created in various organisms, including cereal crops. See, e.g., Shan, Q., et al. *Nature Biotech* 31, 686-688 (2013). Mutation at the break site is introduced through the non-homologous end joining and homology-directed DNA repair pathways.

Induction of specific mutations in the MSD1 homologs from other crop plants is carried out through the introduction of recombinant plasmids expressing the Cas9 nuclease and the sgRNA target that is codon optimized for rice or wheat MSD1 homologs [crispr.mit.edu]. Implementation of the method is through protoplast transformation or by agroinfiltration method with *A. tumufaciens* carrying the binary plasmid harboring the specified target sequence of interest of MSD 1. In protoplast transformation, the two plasmids are co-introduced into the protoplast of callus of crop plants, such as rice or wheat by methods known in the art. See, e.g., Shan, Q., et al, 2013). After the sgRNA binds to the MSD1 homolog, the Cas9 nuclease will be recruited to make specific cut into the homolog and introduce mutations during DNA repair. Introduced mutations in the MSD1 homologs will be screened by PCR and sequencing. Callus that harbor mutations in the MSD1 homolog will be induced to regenerate plants for phenotype evaluation for multiseeded trait.

Example 3

The following example illustrates the conversion and utility of five single nucleotide polymorphisms (SNPs) in the MSD gene as perfect markers for rapid and highly efficient selection of msd trait in three segregating populations of *sorghum*. The msd trait was efficiently introgressed at the $F_2$ generation from cultivar BTx623 into three elite cultivars of *sorghum bicolor* BTx624, RTx430 and RTx437 coupled with KASP SNP assay. The causal SNP markers of msd1 can also be used to efficiently produce elite *sorghum* inbred lines with this trait using a rapid introgression method.

Materials and Methods

Agronomic Aspects
1. Plant Materials and Cultivation

A confirmed mutant of the msd1-1 genotype (BTx623_trsp-12_BC1F3, referred to as msd1-1, aka p12. The cDNA sequence is shown in SEQ ID NO: 5) was crossed to the inbred lines BTx642, RTx430 and RTx437 simultaneously by plastic bag crossing method in field plots maintained at Cropping Systems Research Laboratory, Lubbock, Tex. to create F1 hybrids.

Subsequently, the F1 hybrids were grown in field plots in Mexico, the plants were bagged for self pollination to produce seeds to generate F2 populations. The F2 generation of three populations was grown in field plots at New Deal, Tex.

Four other alleles of msd1: msd1-2 (p15, see SEQ ID NO: 4); msd1-3 (p18, see SEQ ID NO: 6); msd1-4 (p2, see SEQ ID NO: 7) and msd1-5 (p10, see SEQ ID NO: 3) were backcrossed to BTx623 to reduce background mutations. The BC1F2 populations generated from these crosses were analyzed using SNP markers.

2. Phenotyping for msd1

Forty eight F2 offspring from each of three crosses described above were included in the study. Backcross populations of additional msd alleles were examined to verify the msd phenotype. Verification was performed visually by systematic and careful inspection of panicles during flowering and at harvest. Photographs of each panicle were taken. Any panicle with terminal spikes that developed into three seeds, was scored as msd, all others were rated as wild-type (WT).

Molecular Biology and Genomics Aspects
1. Tissue Sampling and Genomic DNA Extraction Leaf samples (200-500 mg) were collected from young seedlings (two to three leaf stage) placed in conical microcentirfuge tubes and freeze dried in a lyophilizer. Genomic DNA (gDNA) was extracted by methods known in the art. See, e.g., Xin and Chen, 2012.

To prepare gDNA for endpoint Kompetitive Allele Specific PCR (KASP) genotyping, 500 ng aliquot of total gDNA was diluted to a concentration of 20 ng/µL with the aid of spectrophotometer, NanoDrop. Diluted DNA samples were stored at −20° C. for late use in endpoint genotyping assay. All genotyping and verification assays were performed on triplicate samples.

2. Development of SNP KASP Markers

The PCR markers for endpoint genotyping using KASP chemistry (LGC Genomics, MA, USA), were designed based on manufacturer's instructions. See, e,g., McCouch. S., et al., *Breeding Science* 60:524 (2010). Briefly, the precise and verified SNP mutation is used to design the KASP endpoint genotyping primer. As disclosed herein single nucleotide polymorphisms (SNPs) give rise to the multi-seeded (msd) phenotype. Knowledge of the sequences of the SNP responsible for the multi-seeded phenotype and the sequences surrounding the SNP permit the design of efficient primers for incorporation of the multi-seeded phenotype into new cultivars.

Primers were designed to include 100-120 nucleotides on each side of the specified SNP, with the actual SNP serving as the center point of the primer sequence. Availability of the correct sequence of the MSD gene is facilitated by Sanger sequencing and is compared to available sequence in databases using BLAST. The list of five KASP primers known as ARSLBK_SNP1 to ARSLBK_SNP5 and their sequences are presented in Table 1 which shows the sequence and information for SNP primers from MSD1 mutations, designed in conjunction with end-point genotyping method with KASP assay for marker assisted introgression and selection to three elite *sorghum bicolor* lines, BTx642, RTx430 and RTx437. The SNP mutation between wild-type (WT) and mutant are indicated in the sequence with brackets and are in bold. Efficiency was based on congruence of genotype and phenotype data.

to make a total of 20 ng/reaction) 5 μl of KASP 2× Mastermix (MM), 0.14 μl of KASP SNP primer (individual/separate assay for (ARSLBK_SNP 1; ARSLBK_SNP2; ARSLBK_SNP3; ARSLK_SNP4; and ARSLBK_SNP5)), and sufficient amount of PCR water to bring reaction volume to ~10 μl.

3. Include negative control wells. Use only water (instead of gDNA solution), need to include 3 wells of negative control per plate.
4. Because of small volumes, it is best to prepare a master mix cocktail for KASP MM, SNP Primer and $H_2O$ (add 9 μl of this MM to white plates) then add gDNA. Remember to:

TABLE 1

| SNP Primer ID | Mutant Target | Sequence (5' to 3') | Marker Efficiency |
|---|---|---|---|
| ARSLBK_SNP1 | msd1-1 (p12) | GCGTCCATGCCGCGGCCGCACCGCGGAAGCGGCCGTTCAGGACGGATCGGCACAGCAAGA TCCGCACGGCGCAGGGCGTGCGCGACCGCC[G/A]GATGCGGCTGTCGGTCGGGGTCGCGC GAGAGTTCTTCGCGCTGCAGGACCGGCTTGGGTTCGACAAGGCCAGCAAGACGGTGAACTG GCTCCTCACCCAGTCCAAGCCGGC (SEQ ID NO: 9) | 100% |
| ARSLBK_SNP2 | msd1-2 (p15) | GCGTCCATGCCGCGGCCGCACCGCGGAAGCGGCCGTTCAGGACGGATCGGCACAGCAAGA TCCGCACGGCGCAGGGCGTGCGCGACCGC[C/T]GGATGCGGCTGTCGGTCGGGGTCGCGC GAGAGTTCTTCGCGCTGCAGGACCGGCTTGGGTTCGACAAGGCCAGCAAGACGGTGAACTG GCTCCTCACCCAGTCCAAGCCGGC (SEQ ID NO: 10) | 100% |
| ARSLBK_SNP3 | msd1-3 (p18) | GACGGATCGGCACAGCAAGATCCGCACGGCGCAGGGCGTGCGCGACCGCCGGATGCGGCT GTCGGTCGGGGTCGCGCGAGAGTTCTTCGCGCTGCAGGACCGGCTTGGGTTCGACAAGGCC AGCAAGA[C/T]GGTGAACTGGCTCCTCACCCAGTCCAAGCCGGCCATCGACCGCCTCGTCGA CGCCGCCGAGCCGGCGGTGGCTCTAGTCTCAGGAGGACCACCGACGGTGGTGAAGGGGAG (SEQ ID NO: 11) | 100% |
| ARSLBK_SNP4 | msd1-4 (p2) | GACGGATCGGCACAGCAAGATCCGCACGGCGCAGGGCGTGCGCGACCGCCGGATGCGGCT GTCGGTCGGGGTCGCGCGAGAGTTCTTCGCGCTGCAGGACCGGCTTGGGTTCGACAAGGCC AGCAAGACGGTGAACTGGCTC[C/T]TCACCCAGTCCAAGCCGGCCATCGACCGCCTCGTCGA CGCCGCCGAGCCGGCGGTGGCTCTAGTCTCAGGAGGACCACCGACGGTGGTGAAGGGGAG AGGGGAGGGGAACTCCTCAAGCACTTGCTGTTTGACGGTGGACTCGAGGGAGGAGGCGAC (SEQ ID NO: 12) | 100% |
| ARSLBK_SNP5 | msd1-5 (p10) | GCCCCTGCAGGCGCCGGCAGCAGCGGGGGAGATGGAGCTGCTGCTGAGGAACGGGTCGCC CGTACCGGTGGTGGATGCCGGCGTCCATGCCGCGGCCGCACCGCGGAAGCGGCCGTTCAG GAC[G/A]GATCGGCACAGCAAGATCCGCACGGCGCAGGGCGTGCGCGACCGCCGGATGCG GCTGTCGGTCGGGGTCGCGCGAGAGTTCTTCGCGCTGCAGGACCGGCTTGGGTTCGACAAG GC (SEQ ID NO: 13) | 100% |

3. Endpoint Genotyping with KASP Assay

Endpoint genotyping using the KASP chemistry involves a two-step PCR assay, a common downstream primer and two competitive upstream primers. Specifically one of the primers will anneal to the wild-type sequence, and the other will anneal to the mutant sequence. For plants that do not harbor the mutation, only the wild-type allele will be amplified. For homozygous mutants, only the mutant allele will be amplified. For heterozygous plants, both alleles will be amplified.

The detection system for differences in SNP with KASP technology utilizes fluorescent resonance energy transfer (FRET), which obviates the need for tedious product separation step. KASP assays were performed using Roche Light Cycler 480 equipped with v1.5 software.

A description of the *sorghum* msd genotyping using KASP chemistry on Roche LC480 is described here in detail, and step by step (see, e.g., Semagn, et al., *Mol. Breeding*, 33:1-14 (2013)).

1. Turn on and warm up Roche LC480 first before proceeding to preparation of reaction mix. Prepare white Roche plates that are compatible for FRET analysis.
2. Prepare the reaction mix (~10 μl total) consisting of the following/per reaction: 1 μl of gDNA (conc. 15-20 ng/μl, i. Always prepare a master mix of KASP 2× primer & SNP primer first beforehand. Turn off light when handling KASP 2× Master Mix, reagents are light sensitive.
    ii. It is advised to dispense Master Mix then add gDNA.
    iii. Be careful of cross contamination, assay is very sensitive.
    iv. Genomic DNA concentration is very important; check gDNA concentration of stock with NanoDrop.

5. Dispense into wells of white Roche 96-well plate specific for Roche LC480 as specified in step 1. Seal with LC480 plastic seal carefully but tightly, prevent spill and cross contamination. Cover or wrap in aluminum foil to prevent light exposure and quenching.
6. Centrifuge at 3200 rpm for 5 min. Cover plates with aluminum foil when transporting.
7. Proceed to operate Roche LC480 machine. Place plate in the plate holder making sure to line up the plate according to notch in plate. Proceed with programming for *sorghum* KASP genotyping assay following the general protocol provided by LGC Genomics, but with the following changes: program for touchdown (program 2: from 65° C. to 57° C., ramp at 0.6° C.) thermocycling (program 3:

target temp. 55° C. for 1 min. for annealing) for 30 cycles and quantification (program 4: 37° C. for 5 min., followed by 37° C. single data acquisition for 1 sec.).

8. Genotype data is obtained using default allele calling software embedded within the endpoint genotyping suite of Roche LC480. Allelic calls are presented in a table or graphical format. Genotyping results are exported as MS Excel file or as pdf for easier handling.

9. Methods for SNP KASP analysis using other FRET compatible machine such as e.g., the ultra-high throughput Fluidigm system can also be used and are known in the art. See, e.g., Smith and Maughan, *Methods in Mol. Bio.* 1245:243-256 (2015).

4. Statistical Analysis

The analyses of phenotypic and genotypic segregation in the three F2 populations and with backcross populations were performed using chi-square goodness of fit test according to given statistical equations for the test (Hartl and Jones, 2005 Genetics: Analysis of genes and genomes (6th edition). Jones and Bartlett Publishers, Sudbury, Mass., pp. 162-165). Additional analysis with studentized t-test, Fisher's exact test and congruence of genotype and phenotype was performed using Excel statistical suite or in JMP software.

Results and Discussion

Introgression of msd into Three Elite Genotypes of *sorghum* and Analysis of Backcrosses The msd trait was successfully introgressed into three elite lines of *sorghum* as shown in the segregation pattern of F2 populations. The results of crosses showed that for F2 populations of msd1-1×RTx430, msd1-1×RTx437, and msd1-1×BTx642, the phenotypic segregation followed an overall 3WT:1msd ratio. See Tables 2A, 2B, and 2C. This segregation pattern is in agreement with previous results indicating that the trait is recessive and is controlled by a single gene (see, e.g., Burow et. al., 2014). The results in this study confirmed previous data on msd genetic analysis, and the results for phenotypic segregation is in complete agreement with theoretical expectation because the msd trait was created through EMS mutation and generally results from mutation of single gene.

TABLE 2A

Chi-square test for goodness of fit to a 3:1 phenotypic segregation ratio in the $F_2$ population of cross between trsp12 (msd1-1) × RTx430.

| Phenotype | Observed | Expected | Chi-square statistics | P value |
|---|---|---|---|---|
| Wild type | 44 | 45 | 0.02 | |
| multiseeded | 16 | 15 | 0.07 | |
| Total | 60 | 60 | 0.09 | P = 0.81 |

TABLE 2B

Chi-square test for goodness of fit to a 3:1 phenotypic segregation ratio in the $F_2$ population of cross between trsp12 (msd1-1) × RTx437.

| Phenotype | Observed | Expected | Chi-square statistics | P value |
|---|---|---|---|---|
| Wild type | 37 | 36 | 0.03 | |
| multiseeded | 11 | 12 | 0.08 | |
| Total | 48 | 48 | 0.11 | P = 0.78 |

TABLE 2C

Chi-square test for goodness of fit to a 3:1 phenotypic segregation ratio in the $F_2$ population of cross between trsp12 (msd1-1) × BTx642.

| Phenotype | Observed | Expected | Chi-square statistics | P value |
|---|---|---|---|---|
| Wild type | 31 | 30 | 0.03 | |
| multiseeded | 9 | 10 | 1.00 | |
| Total | 40 | 40 | 1.03 | P = 0.46 |

Utility of SNP Markers

The genotype data for 48 individuals from an F2 population of BTX623_trsp-12_BC1F3×RTx437 are presented in Table 3.

TABLE 3

Analysis of genotype segregation for an $F_2$ population of cross between trsp12 (msd1-1) × RTx437.

| Phenotype | Genotype (SNP) | Observed | Expected | Chi-square statistics | P value |
|---|---|---|---|---|---|
| Wild type | Homozygous (GG) | 12 | 12 | ~ | |
| | Heterozygous (GA) | 25 | 24 | 0.04 | |
| multiseeded | Homozygous (AA) | 11 | 12 | 0.08 | |
| Total | | 48 | 48 | 0.12 | P = 0.96 (df = 2) |

The overall segregation ratio for the population was 1WT:2Het:1msd. Translated into actual SNP variation: 1GG (WT):2GA(Heterozygotes):1AA (Mutants). Table 4 shows genotype and phenotype data for each individual for msd1-1×RTx437 presented. Furthermore all F2 plants of this population that genotyped at very early stage as homozygous mutants (AA) had the msd1 phenotype at anthesis and in mature panicle. Accurate congruence between genotype and phenotype data was observed for backcross population individuals tested. The analysis was performed at seedling stage, indicating the utility of the SNP markers can allow for savings in labor, time and space for analysis.

TABLE 4

Individual phenotype and genotype data for 48 individuals in an $F_2$ population of cross trsp12 (msd1-1) × RTx437

| Pedigree and $F_2$ ID | Phenotype | SNP Genotype | Genotypic state |
|---|---|---|---|
| (BC1F3Triseed_BTx623*RTx437)-F2-1 | WT | GA | Heterozygote WT |
| (BC1F3Triseed_BTx623*RTx437)-F2-2 | WT | GA | Heterozygote WT |
| (BC1F3Triseed_BTx623*RTx437)-F2-3 | WT | GA | Heterozygote WT |

TABLE 4-continued

Individual phenotype and genotype data for 48 individuals
in an F₂ population of cross trsp12 (msd1-1) × RTx437

| Pedigree and F₂ ID | Phenotype | SNP Genotype | Genotypic state |
|---|---|---|---|
| (BC1F3Triseed_BTx623*RTx437)-F2-4 | WT | GG | Homozygote WT |
| (BC1F3Triseed_BTx623*RTx437)-F2-5 | WT | GG | Homozygote WT |
| (BC1F3Triseed_BTx623*RTx437)-F2-6 | WT | GG | Homozygote WT |
| (BC1F3Triseed_BTx623*RTx437)-F2-7 | WT | GG | Homozygote WT |
| (BC1F3Triseed_BTx623*RTx437)-F2-8 | WT | GA | Heterozygote WT |
| (BC1F3Triseed_BTx623*RTx437)-F2-9 | WT | GG | Homozygote WT |
| (BC1F3Triseed_BTx623*RTx437)-F2-10 | WT | GA | Heterozygote WT |
| (BC1F3Triseed_BTx623*RTx437)-F2-11 | WT | GG | Homozygote WT |
| (BC1F3Triseed_BTx623*RTx437)-F2-12 | WT | GA | Heterozygote WT |
| (BC1F3Triseed_BTx623*RTx437)-F2-13 | WT | GA | Heterozygote WT |
| (BC1F3Triseed_BTx623*RTx437)-F2-14 | WT | GA | Heterozygote WT |
| (BC1F3Triseed_BTx623*RTx437)-F2-15 | msd | AA | Homozygote mutant |
| (BC1F3Triseed_BTx623*RTx437)-F2-16 | WT | GA | Heterozygote WT |
| (BC1F3Triseed_BTx623*RTx437)-F2-17 | WT | GA | Heterozygote WT |
| (BC1F3Triseed_BTx623*RTx437)-F2-18 | WT | GA | Heterozygote WT |
| (BC1F3Triseed_BTx623*RTx437)-F2-19 | msd | AA | Homozygote mutant |
| (BC1F3Triseed_BTx623*RTx437)-F2-20 | WT | GG | Homozygote WT |
| (BC1F3Triseed_BTx623*RTx437)-F2-21 | WT | GG | Homozygote WT |
| (BC1F3Triseed_BTx623*RTx437)-F2-22 | WT | GA | Heterozygote WT |
| (BC1F3Triseed_BTx623*RTx437)-F2-23 | msd | AA | Homozygote mutant |
| (BC1F3Triseed_BTx623*RTx437)-F2-24 | WT | GA | Heterozygote WT |
| (BC1F3Triseed_BTx623*RTx437)-F2-25 | msd | AA | Homozygote mutant |
| (BC1F3Triseed_BTx623*RTx437)-F2-26 | WT | GG | Heterozygote WT |
| (BC1F3Triseed_BTx623*RTx437)-F2-27 | WT | GG | Heterozygote WT |
| (BC1F3Triseed_BTx623*RTx437)-F2-28 | msd | AA5 | Homozygote mutant |
| (BC1F3Triseed_BTx623*RTx437)-F2-29 | WT | GG | Heterozygote WT |
| (BC1F3Triseed_BTx623*RTx437)-F2-30 | msd | AA6 | Homozygote mutant |
| (BC1F3Triseed_BTx623*RTx437)-F2-31 | WT | GG | Heterozygote WT |
| (BC1F3Triseed_BTx623*RTx437)-F2-32 | WT | GA | Heterozygote WT |
| (BC1F3Triseed_BTx623*RTx437)-F2-33 | WT | GA | Heterozygote WT |
| (BC1F3Triseed_BTx623*RTx437)-F2-34 | WT | GA | Heterozygote WT |
| (BC1F3Triseed_BTx623*RTx437)-F2-35 | WT | GA | Heterozygote WT |
| (BC1F3Triseed_BTx623*RTx437)-F2-36 | WT | GA | Heterozygote WT |
| (BC1F3Triseed_BTx623*RTx437)-F2-37 | WT | GA | Heterozygote WT |
| (BC1F3Triseed_BTx623*RTx437)-F2-38 | WT | GA | Heterozygote WT |
| (BC1F3Triseed_BTx623*RTx437)-F2-39 | msd | AA | Homozygote mutant |
| (BC1F3Triseed_BTx623*RTx437)-F2-40 | WT | GA | Heterozygote WT |
| (BC1F3Triseed_BTx623*RTx437)-F2-41 | msd | AA | Homozygote mutant |
| (BC1F3Triseed_BTx623*RTx437)-F2-42 | msd | AA | Homozygote mutant |
| (BC1F3Triseed_BTx623*RTx437)-F2-43 | WT | GA | Heterozygote WT |
| (BC1F3Triseed_BTx623*RTx437)-F2-44 | WT | GA | Heterozygote WT |
| (BC1F3Triseed_BTx623*RTx437)-F2-45 | msd | AA | Homozygote mutant |
| (BC1F3Triseed_BTx623*RTx437)-F2-46 | WT | GA | Heterozygote WT |
| (BC1F3Triseed_BTx623*RTx437)-F2-47 | WT | GA | Heterozygote WT |
| (BC1F3Triseed_BTx623*RTx437)-F2-48 | msd | AA | Homozygote mutant |

Use of an msd SNP_KASP marker allows one to differentiate homozygous wild type from heterozygote in the "mixed" group of F2s that visually exhibit wild type feature (MSD). This applicability to differentiate heterozygote from homozygous facilitates rapid introgression aspects of the methods disclosed herein.

Application of msd1 SNP Markers Coupled With Endpoint Genotyping for Rapid Introgression of Trait For Swifter Production of *sorghum* Inbred Lines.

With the causal mutations for several alleles of msd1 identified, molecular mark were designed based on the mutations in the MSD1 gene as described above and demonstrated its accuracy and utility. These markers can be used for a highly efficient breeding approach referred to as Marker Assisted Rapid Trait Introgression (MARTI). MARTI for msd trait combines precise SNP, specifically the mutations disclosed for msd1 gene, with a modified backcrossing approach. An illustration of the method is shown in FIG. 5. Briefly, (1) the approach involves the creation of primary crosses between a homozygous msd1 plant (msd1-1) and an elite line (or two or more lines) of interest for introgression to obtain F1 offspring. The F1 generation is heterozygous for msd trait. (2) Subsequently, an F1 plant will be backcrossed to the elite parent producing BC1F1 which genetically will produce 50% WT and 5% heterozygote msd. (3) At this stage of introgression, precise msd SNP marker will be used to select the heterozygotes harboring the msd mutation among WT looking plants using ARSLBK_SNP1 primer coupled with Kompetitive Allele Specific PCR (KASP) assay. KASP assay is known in the art. See, e.g., Semagn, et al. (2014). (4) Selected heterozygotes will be backcrossed to the elite line to perform further introgression. (5) This process of MARTI can be performed for another four cycles and (6) finally self-pollinated by bagging to produce BC6F2 generation. The BC6F2 generation is expected to give a phenotypic segregation ratio of 3WT:1 msd. (7) Selection for msd plants at the BC6F2 generation can be facilitated at the seedling stage using ARSLBK_SNP1 primer coupled with Kompetitive Allele Specific PCR (KASP) assay, combined with phenotypic selection at maturity. These cycles of crossing and selection can be achieved in a span of 2 to 2.5 years, as compared to 6 years for conventional backcrossing introgression method now in use. Thus, the application of MARTI using msd SNP markers significantly reduced the time to introgress the msd1 mutations into an elite lines for producing commercial hybrids.

The final product will be an inbred line almost identical (99%) to the original elite inbred parent that has the homozygous state for the msd gene and trait. As proposed, the application of msd single nucleotide mutations will greatly accelerate the introgression of msd1 trait into all elite lines and increase the overall throughput of breeding program. Because all msd1 mutations are recessive, it is necessary to introduce the mutation into both parents to create commercial hybrids with msd1 trait. Simultaneous introgression can be accomplished through MARTI of msd trait using ARSLBK_SNP1 primer or other primers (ARSLBK_SNP2 to 5 or the primers listed in Table 9, infra) coupled with Kompetitive Allele Specific PCR (KASP) and development of inbred lines achieved within 2-2,5 years.

Example 4

The following example illustrates the development of exemplary multi-seeded (msd) breeding lines of sorghum using marker assisted selection and the msd alleles disclosed herein.

Multi-Seeded Breeding Lines of Sorghum

The multi-seeded (msd) breeding lines: B.14001msd1-1, R.14004msd1-1 and R.14007msd1-1 are grain sorghum (Sorghum bicolor M.) inbreds developed at the Cropping Systems Research Laboratory, USDA-ARS in Lubbock, Tex.

The pedigree of B.14001msd1-1 is: B.Tx623p12msd X B.Tx642. B.Tx623p12msd is an msd mutant line developed at CSRL, USDA-ARS. B.Tx642 is a publicly available line developed by Texas A&M University.

The pedigree of R.14004msd1-1 is: B.Tx623p12msd X R.Tx437. B.Tx623p12msd is an msd mutant line developed at CSRL, USDA-ARS. R.Tx437 is a publicly available line developed by Texas A&M University.

The pedigree of R.14007msd.1-1 is: B.Tx623p12msd X R.Tx430. B.Tx623p12msd is an msd mutant line developed at CSRL, USDA-ARS. R.Tx430 is a publicly available line developed by Texas A&M University.

Pedigree and Breeding to Obtain Exemplary Multi-Seeded Sorghum Breeding Lines

The pedigree method of breeding was used in the development of B.14001msd1-1, R.14004msd1-1 and R.14007msd1-1 as per the following:

The F1 cross was made at USDA's research location in Lubbock, Tex., during the summer of 2012. The F2 seed was obtained during the winter of 2012-13 in a winter nursery in Puerto Vallarta, MX. The F2 population was grown in Lubbock, Tex., during the summer of 2013, and seed from 40 heads phenotypically classified as msd and genetically classified as msd (as discussed in Example 3) from the segregation population were bulked together. All plants were self-pollinated. The F3 population consisting of msd plants was grown in a winter nursery (2013-2014) in Puerto Vallarta, MX. A total of 50 msd plants per F3 population were selected. All plants were self-pollinated. The F4 families were grown head to row in Lubbock, Tex., in the summer of 2014, and one head was taken from selected rows. The F5 generation was grown and bulked in Guayanilla, PR, in the winter of 2014-2015. The lines created were visually confirmed to be true breeding msd in 2015. The criteria for selection at each generation are shown in Tables 5, 6, 7, and 8 below.

TABLE 5

Breeding History of B.14001msd1-1

| Season/Year | Inbreeding | Research Location | Pedigree | Heads Selected |
|---|---|---|---|---|
| S/2012 | $F_0$ | Lubbock, Texas | B.Tx623p12msd/B.Tx642 | |
| W/2012-13 | $F_1$ | Puerto Vallarta, Mexico | (B.Tx623p12msd/B.Tx642) | Bulk |
| S/2013 | $F_2$ | Lubbock, Texas | (B.Tx623p12msd/B.Tx642)-F2 | 40 |
| W/2013-14 | $F_3$ | Puerto Vallarta, Mexico | (B.Tx623p12msd/B.Tx642)-F2-F3 | 50 |
| S/2014 | $F_4$ | Lubbock, Texas | (B.Tx623p12msd/B.Tx642)-F2-F3-12 | 1 |
| W/2014-15 | $F_5$ | Guayanilla, Puerto Rico | (B.Tx623p12msd/B.Tx642)-F2-F3-12-1 | Bulk |

TABLE 6

Breeding History of R.14004msd1-1

| Season/Year | Inbreeding | Research Location | Pedigree | Heads Selected |
|---|---|---|---|---|
| S/2012 | $F_0$ | Lubbock, Texas | B.Tx623p12msd/R.Tx437 | |
| W/2012-13 | $F_1$ | Puerto Vallarta, Mexico | (B.Tx623p12msd/R.Tx437) | Bulk |
| S/2013 | $F_2$ | Lubbock, Texas | (B.Tx623p12msd/R.Tx437)-F2 | 40 |
| W/2013-14 | $F_3$ | Puerto Vallarta, Mexico | (B.Tx623p12msd/R.Tx437)-F2-F3 | 50 |
| S/2014 | $F_4$ | Lubbock, Texas | (B.Tx623p12msd/R.Tx437)-F2-F3-30 | 1 |
| W/2014-15 | $F_5$ | Guayanilla, Puerto Rico | (B.Tx623p12msd/R.Tx437)-F2-F3-30-1 | Bulk |

TABLE 7

Breeding History of R.14007msd1-1

| Season/Year | Inbreeding | Research Location | Pedigree | Heads Selected |
|---|---|---|---|---|
| S/2012 | $F_0$ | Lubbock, Texas | B.Tx623p12msd/R.Tx430 | |
| W/2012-13 | $F_1$ | Puerto Vallarta, Mexico | (B.Tx623p12msd/R.Tx430) | Bulk |
| S/2013 | $F_2$ | Lubbock, Texas | (B.Tx623p12msd/R.Tx430)-F2 | 40 |
| W/2013-14 | $F_3$ | Puerto Vallarta, Mexico | (B.Tx623p12msd/R.Tx430)-F2-F3 | 50 |
| S/2014 | $F_4$ | Lubbock, Texas | (B.Tx623p12msd/R.Tx430)-F2-F3-36 | 1 |
| W/2014-15 | $F_5$ | Guayanilla, Puerto Rico | (B.Tx623p12msd/R.Tx430)-F2-F3-36-1 | Bulk |

TABLE 8

Selection criteria for B.14001msd1-1, R.14004msd1-1 and R.14007msd1-1

| Generation | Traits segregating | Selection Criteria |
|---|---|---|
| $F_1$ | Hybrid or inbred plants | Select F1 hybrids with markers or phenotype |
| $F_2$ | msd, height, maturity | msd marker, moderate height, 50-70 DAP anthesis |
| $F_3$ | Head type, maturity | semi-open head, early maturity |
| $F_4$ | Head type, uniformity | Representative head |
| $F_5$ | Uniformity, visual confirmation of msd | Bulk random heads |

In addition to the primers listed supra, the SNP primers listed in Table 9, infra, can be used to identify plants containing the MSD1 mutations. These primers have been validated for the indicated alleles and are compatible with KASP protocols described supra. These primers can be chemically synthesized.

It is understood that the examples and embodiments described herein are for illustrative purposes only and that various modifications or changes in light thereof will be suggested to persons skilled in the art and are to be included within the spirit and purview of this application and scope of the appended claims.

TABLE 9

| GENE ID | Primer_ID | Allele_X (5' to 3') (forward primer) | Allele_Y (5' to 3') (forward primer) | Common (5' to 3') (reverse primer) |
|---|---|---|---|---|
| Sb07g021140 | LBK_ARS_Msd1-1 | CCGACAGCCGCATCC (SEQ ID NO: 17) (Wild type) | GACCGACAGCCGCATCT (SEQ ID NO: 18)(Mutant p12) | ATCGGCACAGCAAGATCC (SEQ ID NO: 19) |
| Sb07g021140 | LBK_ARS_Msd1-2 | CCGACAGCCGCATCGA (SEQ ID NO: 20) (Mutant p15) | CCGACAGCCGCATCGG (SEQ ID NO: 21) (Wild type) | ATCGGCACAGCAAGATCC (SEQ ID NO: 22) |
| Sb07g021140 | LBK_ARS_Msd1-3 | CGACAAGGCCAGCAAGAT (SEQ ID NO: 23) (Mutant p18) | CGACAAGGCCAGCAAGAC (SEQ ID NO: 24) (Wild type) | CGGTGGTCCTCCTGAGACT (SEQ ID NO: 25) |
| Sb07g021140 | LBK_ARS_Msd1-4 | CAAGACGGTGAACTGGCTCT (SEQ ID NO: 26)(Mutant p2) | AAGACGGTGAACTGGCTCC (SEQ ID NO: 27)(Wild type) | CGGTGGTCCTCCTGAGACT (SEQ ID NO: 28) |
| Sb07g021140 | LBK_ARS_Msd1-5 | GGATCTTGCTGTGCCGATT (SEQ ID NO: 14) (Mutant p10) | GGATCTTGCTGTGCCGATC (SEQ ID NO: 15)(Wild type) | GAGATGGAGCTGCTGCTGA (SEQ ID NO: 16) |

We, the inventors, claim as follows:

1. A genetically altered *sorghum* plant having a multi-seeded phenotype wherein the genetically altered *sorghum* plant produces a mutated MSD1 protein comprising an amino acid sequence selected from the group consisting of SEQ ID NOs: 30, 31, 32, 33, 34, 35, and 36.

2. A seed from the genetically altered *sorghum* plant of claim 1 wherein the seed comprises a polynucleotide encoding said mutated MSD1 protein.

3. A genetically altered *sorghum* plant produced by growing the seed of claim 2.

4. A tissue culture of regenerable cells produced from the genetically altered *sorghum* plant having the multi-seeded phenotype of claim 1.

5. An oil from the seed of claim 2, wherein said oil contains the polynucleotide encoding said mutated MSD1 protein.

* * * * *

SEQUENCE LISTING

<160> NUMBER OF SEQ ID NOS: 36

<210> SEQ ID NO 1
<211> LENGTH: 774
<212> TYPE: DNA
<213> ORGANISM: Sorghum bicolor

<400> SEQUENCE: 1

```
atgccgtcga ccgcgatgtc ttgggacggg tacggcgggc agatcttccc cgccgacatg    60
tcgtcgttcc accaccagga caccctggag gccgtgttcc ggcagcctga dacgacggcg   120
cccctgcagg cgccggcagc agcggggggag atggagctgc tgctgaggaa cgggtcgccc   180
gtaccggtgg tggatgccgg cgtccatgcc gcggccgcac cgcggaagcg gccgttcagg   240
acggatcggc acagcaagat ccgcacggcg cagggcgtgc gcgaccgccg gatgcggctg   300
tcggtcgggg tcgcgcgaga gttcttcgcg ctgcaggacc ggcttgggtt cgacaaggcc   360
agcaagacgg tgaactggct cctcacccag tccaagccgg ccatcgaccg cctcgtcgac   420
gccgccgagc cggcggtggc tctagtctca ggaggaccac cgacggtggt gaaggggaga   480
ggggagggga actcctcaag cacttgctgt ttgacggtgg actcgaggga ggaggcgacg   540
gagaaggcaa gaagcagagg cggcggcggc ggcggtaccg gtggtcctga tgggccaccg   600
gcgctcatgg aagaacacgg ccgcggtgag ctgggctgga tcatgacgga ggccacagcg   660
gcagcggcgg cagcaacggc gcagccgcag cagatggacg ggctggagta ctactaccag   720
tattgcctgc agctcgagga gatgatgaga tgcaacggag gaatgccaag gtga         774
```

<210> SEQ ID NO 2
<211> LENGTH: 774
<212> TYPE: DNA
<213> ORGANISM: Sorghum bicolor

<400> SEQUENCE: 2

```
atgccgtcga ccgcgatgtc ttgggacggg tacggcgggc agatcttccc cgccgacatg    60
tcgtcgttcc accaccagga caccctggag gccgtgttcc ggcagcctga dacgacggcg   120
cccctgcagg cgccggcagc agcggggggag atggagctgc tgctgaggaa cgggtcgccc   180
gtaccggtgg tggatgccgg cgtccatgcc gcggccgcac cgcggaagca gccgttcagg   240
acggatcggc acagcaagat ccgcacggcg cagggcgtgc gcgaccgccg gatgcggctg   300
tcggtcgggg tcgcgcgaga gttcttcgcg ctgcaggacc ggcttgggtt cgacaaggcc   360
agcaagacgg tgaactggct cctcacccag tccaagccgg ccatcgaccg cctcgtcgac   420
gccgccgagc cggcggtggc tctagtctca ggaggaccac cgacggtggt gaaggggaga   480
ggggagggga actcctcaag cacttgctgt ttgacggtgg actcgaggga ggaggcgacg   540
gagaaggcaa gaagcagagg cggcggcggc ggcggtaccg gtggtcctga tgggccaccg   600
gcgctcatgg aagaacacgg ccgcggtgag ctgggctgga tcatgacgga ggccacagcg   660
gcagcggcgg cagcaacggc gcagccgcag cagatggacg ggctggagta ctactaccag   720
tattgcctgc agctcgagga gatgatgaga tgcaacggag gaatgccaag gtga         774
```

<210> SEQ ID NO 3
<211> LENGTH: 774
<212> TYPE: DNA
<213> ORGANISM: Sorghum bicolor

<400> SEQUENCE: 3

```
atgccgtcga ccgcgatgtc ttgggacggg tacggcgggc agatcttccc cgccgacatg    60
```

```
tcgtcgttcc accaccagga caccctggag gccgtgttcc ggcagcctga gacgacggcg      120
cccctgcagg cgccggcagc agcggggag atggagctgc tgctgaggaa cgggtcgccc       180
gtaccggtgg tggatgccgg cgtccatgcc gcggccgcac cgcggaagcg gccgttcagg      240
acgaatcggc acagcaagat ccgcacggcg cagggcgtgc gcgaccgccg gatgcggctg      300
tcggtcgggg tcgcgcgaga gttcttcgcg ctgcaggacc ggcttgggtt cgacaaggcc      360
agcaagacgg tgaactggct cctcacccag tccaagccgg ccatcgaccg cctcgtcgac      420
gccgccgagc cggcggtggc tctagtctca ggaggaccac cgacggtggt gaaggggaga      480
ggggagggga actcctcaag cacttgctgt ttgacggtgg actcgaggga ggaggcgacg      540
gagaaggcaa gaagcagagg cggcggcggc ggcggtaccg gtggtcctga tgggccaccg      600
gcgctcatgg aagaacacgg ccgcggtgag ctgggctgga tcatgacgga ggccacagcg      660
gcagcggcgg cagcaacggc gcagccgcag cagatggacg ggctggagta ctactaccag      720
tattgcctgc agctcgagga gatgatgaga tgcaacggag gaatgccaag gtga           774
```

<210> SEQ ID NO 4
<211> LENGTH: 774
<212> TYPE: DNA
<213> ORGANISM: Sorghum bicolor

<400> SEQUENCE: 4

```
atgccgtcga ccgcgatgtc ttgggacggg tacggcgggc agatcttccc cgccgacatg       60
tcgtcgttcc accaccagga caccctggag gccgtgttcc ggcagcctga gacgacggcg      120
cccctgcagg cgccggcagc agcggggag atggagctgc tgctgaggaa cgggtcgccc       180
gtaccggtgg tggatgccgg cgtccatgcc gcggccgcac cgcggaagcg gccgttcagg      240
acggatcggc acagcaagat ccgcacggcg cagggcgtgc gcgaccgctg gatgcggctg      300
tcggtcgggg tcgcgcgaga gttcttcgcg ctgcaggacc ggcttgggtt cgacaaggcc      360
agcaagacgg tgaactggct cctcacccag tccaagccgg ccatcgaccg cctcgtcgac      420
gccgccgagc cggcggtggc tctagtctca ggaggaccac cgacggtggt gaaggggaga      480
ggggagggga actcctcaag cacttgctgt ttgacggtgg actcgaggga ggaggcgacg      540
gagaaggcaa gaagcagagg cggcggcggc ggcggtaccg gtggtcctga tgggccaccg      600
gcgctcatgg aagaacacgg ccgcggtgag ctgggctgga tcatgacgga ggccacagcg      660
gcagcggcgg cagcaacggc gcagccgcag cagatggacg ggctggagta ctactaccag      720
tattgcctgc agctcgagga gatgatgaga tgcaacggag gaatgccaag gtga           774
```

<210> SEQ ID NO 5
<211> LENGTH: 774
<212> TYPE: DNA
<213> ORGANISM: Sorghum bicolor

<400> SEQUENCE: 5

```
atgccgtcga ccgcgatgtc ttgggacggg tacggcgggc agatcttccc cgccgacatg       60
tcgtcgttcc accaccagga caccctggag gccgtgttcc ggcagcctga gacgacggcg      120
cccctgcagg cgccggcagc agcggggag atggagctgc tgctgaggaa cgggtcgccc       180
gtaccggtgg tggatgccgg cgtccatgcc gcggccgcac cgcggaagcg gccgttcagg      240
acggatcggc acagcaagat ccgcacggcg cagggcgtgc gcgaccgcca gatgcggctg      300
tcggtcgggg tcgcgcgaga gttcttcgcg ctgcaggacc ggcttgggtt cgacaaggcc      360
```

| | |
|---|---|
| agcaagacgg tgaactggct cctcacccag tccaagccgg ccatcgaccg cctcgtcgac | 420 |
| gccgccgagc cggcggtggc tctagtctca ggaggaccac cgacggtggt gaaggggaga | 480 |
| ggggagggga actcctcaag cacttgctgt ttgacggtgg actcgaggga ggaggcgacg | 540 |
| gagaaggcaa gaagcagagg cggcggcggc ggcggtaccg gtggtcctga tgggccaccg | 600 |
| gcgctcatgg aagaacacgg ccgcggtgag ctgggctgga tcatgacgga ggccacagcg | 660 |
| gcagcggcgg cagcaacggc gcagccgcag cagatggacg ggctggagta ctactaccag | 720 |
| tattgcctgc agctcgagga gatgatgaga tgcaacggag gaatgccaag gtga | 774 |

<210> SEQ ID NO 6
<211> LENGTH: 774
<212> TYPE: DNA
<213> ORGANISM: Sorghum bicolor

<400> SEQUENCE: 6

| | |
|---|---|
| atgccgtcga ccgcgatgtc ttgggacggg tacggcgggc agatcttccc cgccgacatg | 60 |
| tcgtcgttcc accaccagga caccctggag gccgtgttcc ggcagcctga gacgacggcg | 120 |
| cccctgcagg cgccggcagc agcggggggag atggagctgc tgctgaggaa cgggtcgccc | 180 |
| gtaccggtgg tggatgccgg cgtccatgcc gcggccgcac cgcggaagcg gccgttcagg | 240 |
| acggatcggc acagcaagat ccgcacggcg cagggcgtgc cgaccgccg gatgcggctg | 300 |
| tcggtcgggg tcgcgcgaga gttcttcgcg ctgcaggacc ggcttgggtt cgacaaggcc | 360 |
| agcaagatgg tgaactggct cctcacccag tccaagccgg ccatcgaccg cctcgtcgac | 420 |
| gccgccgagc cggcggtggc tctagtctca ggaggaccac cgacggtggt gaaggggaga | 480 |
| ggggagggga actcctcaag cacttgctgt ttgacggtgg actcgaggga ggaggcgacg | 540 |
| gagaaggcaa gaagcagagg cggcggcggc ggcggtaccg gtggtcctga tgggccaccg | 600 |
| gcgctcatgg aagaacacgg ccgcggtgag ctgggctgga tcatgacgga ggccacagcg | 660 |
| gcagcggcgg cagcaacggc gcagccgcag cagatggacg ggctggagta ctactaccag | 720 |
| tattgcctgc agctcgagga gatgatgaga tgcaacggag gaatgccaag gtga | 774 |

<210> SEQ ID NO 7
<211> LENGTH: 774
<212> TYPE: DNA
<213> ORGANISM: Sorghum bicolor

<400> SEQUENCE: 7

| | |
|---|---|
| atgccgtcga ccgcgatgtc ttgggacggg tacggcgggc agatcttccc cgccgacatg | 60 |
| tcgtcgttcc accaccagga caccctggag gccgtgttcc ggcagcctga gacgacggcg | 120 |
| cccctgcagg cgccggcagc agcggggggag atggagctgc tgctgaggaa cgggtcgccc | 180 |
| gtaccggtgg tggatgccgg cgtccatgcc gcggccgcac cgcggaagcg gccgttcagg | 240 |
| acggatcggc acagcaagat ccgcacggcg cagggcgtgc cgaccgccg gatgcggctg | 300 |
| tcggtcgggg tcgcgcgaga gttcttcgcg ctgcaggacc ggcttgggtt cgacaaggcc | 360 |
| agcaagacgg tgaactggct cttcacccag tccaagccgg ccatcgaccg cctcgtcgac | 420 |
| gccgccgagc cggcggtggc tctagtctca ggaggaccac cgacggtggt gaaggggaga | 480 |
| ggggagggga actcctcaag cacttgctgt ttgacggtgg actcgaggga ggaggcgacg | 540 |
| gagaaggcaa gaagcagagg cggcggcggc ggcggtaccg gtggtcctga tgggccaccg | 600 |
| gcgctcatgg aagaacacgg ccgcggtgag ctgggctgga tcatgacgga ggccacagcg | 660 |
| gcagcggcgg cagcaacggc gcagccgcag cagatggacg ggctggagta ctactaccag | 720 | tattgcctgc agctcgagga gatgatgaga tgcaacggag gaatgccaag gtga      774

<210> SEQ ID NO 8
<211> LENGTH: 639
<212> TYPE: DNA
<213> ORGANISM: Sorghum bicolor

<400> SEQUENCE: 8
atgccgtcga ccgcgatgtc ttgggacggg tacggcgggc agatcttccc cgccgacatg      60
tcgtcgttcc accaccagga caccctggag gccgtgttcc ggcagcctga gacgacggcg     120
cccctgcagg cgccggcagc agcggggag atggagctgc tgctgaggaa cgggtcgccc     180
gtaccggtgg tggatgccgg cgtccatgcc gcggccgcac cgcggaagcg gccgttcagg     240
acggatcggc acagcaagat ccgcacggcg cagggcgtgc gcgaccgccg gatgcggctg     300
tcggtcgggg tcgcgcgaga gttcttcgcg ctgcaggacc ggcttgggtt cgacaaggcc     360 agcaagacg tgaactggct cctcacccag tccaagccgg ccatcgaccg cctcgtcgac     420
gccgccgagc cggcggtggc tctagtctca ggaggaccac cgacggtggt gaaggggaga     480
ggggagggga actcctcaag cacttgctgt ttgacggtgg actcgaggga ggaggcgacg     540
gagaaggcaa gaagcagagg cggcggcggc ggcggtaccg gtggtcctga tgggccaccg     600
gcgctcatgg aagaacacgg ccgcggtgag ctgggctga                            639

<210> SEQ ID NO 9
<211> LENGTH: 202
<212> TYPE: DNA
<213> ORGANISM: Artificial Sequence
<220> FEATURE:
<223> OTHER INFORMATION: Primer

<400> SEQUENCE: 9
gcgtccatgc cgcggccgca ccgcggaagc ggccgttcag gacggatcgg cacagcaaga      60
tccgcacggc gcagggcgtg cgcgaccgcc rgatgcggct gtcggtcggg gtcgcgcgag     120
agttcttcgc gctgcaggac cggcttgggt tcgacaaggc cagcaagacg gtgaactggc     180
tcctcaccca gtccaagccg gc                                              202

<210> SEQ ID NO 10
<211> LENGTH: 202
<212> TYPE: DNA
<213> ORGANISM: Artificial Sequence
<220> FEATURE:
<223> OTHER INFORMATION: Primer

<400> SEQUENCE: 10
gcgtccatgc cgcggccgca ccgcggaagc ggccgttcag gacggatcgg cacagcaaga      60
tccgcacggc gcagggcgtg cgcgaccgcy ggatgcggct gtcggtcggg gtcgcgcgag     120
agttcttcgc gctgcaggac cggcttgggt tcgacaaggc cagcaagacg gtgaactggc     180
tcctcaccca gtccaagccg gc                                              202

<210> SEQ ID NO 11
<211> LENGTH: 240
<212> TYPE: DNA
<213> ORGANISM: Artificial Sequence
<220> FEATURE:
<223> OTHER INFORMATION: Primer

<400> SEQUENCE: 11
gacggatcgg cacagcaaga tccgcacggc gcagggcgtg cgcgaccgcc ggatgcggct    60
gtcggtcggg gtcgcgcgag agttcttcgc gctgcaggac cggcttgggt tcgacaaggc   120
cagcaagayg gtgaactggc tcctcaccca gtccaagccg gccatcgacc gcctcgtcga   180
cgccgccgag ccggcggtgg ctctagtctc aggaggacca ccgacggtgg tgaaggggag   240

<210> SEQ ID NO 12
<211> LENGTH: 300
<212> TYPE: DNA
<213> ORGANISM: Artificial Sequence
<220> FEATURE:
<223> OTHER INFORMATION: Primer

<400> SEQUENCE: 12
gacggatcgg cacagcaaga tccgcacggc gcagggcgtg cgcgaccgcc ggatgcggct    60
gtcggtcggg gtcgcgcgag agttcttcgc gctgcaggac cggcttgggt tcgacaaggc   120
cagcaagacg gtgaactggc tcytcaccca gtccaagccg gccatcgacc gcctcgtcga   180
cgccgccgag ccggcggtgg ctctagtctc aggaggacca ccgacggtgg tgaaggggag   240
aggggagggg aactcctcaa gcacttgctg tttgacggtg gactcgaggg aggaggcgac   300

<210> SEQ ID NO 13
<211> LENGTH: 240
<212> TYPE: DNA
<213> ORGANISM: Artificial Sequence
<220> FEATURE:
<223> OTHER INFORMATION: Primer

<400> SEQUENCE: 13
gccnctgcag gcgccggcag cagcggggga gatggagctg ctgctgagga acgggtcgcc    60
cgtaccggtg gtggatgccg gcgtccatgc cgcggccgca ccgcggaagc ggccgttcag   120
gacrgatcgg cacagcaaga tccgcacggc gcagggcgtg cgcgaccgcc ggatgcggct   180
gtcggtcggg gtcgcgcgag agttcttcgc gctgcaggac cggcttgggt tcgacaaggc   240

<210> SEQ ID NO 14
<211> LENGTH: 19
<212> TYPE: DNA
<213> ORGANISM: Artificial Sequence
<220> FEATURE:
<223> OTHER INFORMATION: Primer

<400> SEQUENCE: 14
ggatcttgct gtgccgatt                                                  19

<210> SEQ ID NO 15
<211> LENGTH: 19
<212> TYPE: DNA
<213> ORGANISM: Artificial Sequence
<220> FEATURE:
<223> OTHER INFORMATION: Primer

<400> SEQUENCE: 15
ggatcttgct gtgccgatc                                                  19

<210> SEQ ID NO 16
<211> LENGTH: 19
<212> TYPE: DNA
<213> ORGANISM: Artificial Sequence
<220> FEATURE:
<223> OTHER INFORMATION: Primer

<400> SEQUENCE: 16
gagatggagc tgctgctga                                        19

<210> SEQ ID NO 17
<211> LENGTH: 15
<212> TYPE: DNA
<213> ORGANISM: Artificial Sequence
<220> FEATURE:
<223> OTHER INFORMATION: Primer

<400> SEQUENCE: 17
ccgacagccg catcc                                            15

<210> SEQ ID NO 18
<211> LENGTH: 17
<212> TYPE: DNA
<213> ORGANISM: Artificial Sequence
<220> FEATURE:
<223> OTHER INFORMATION: Primer

<400> SEQUENCE: 18
gaccgacagc cgcatct                                          17

<210> SEQ ID NO 19
<211> LENGTH: 18
<212> TYPE: DNA
<213> ORGANISM: Artificial Sequence
<220> FEATURE:
<223> OTHER INFORMATION: Primer

<400> SEQUENCE: 19
atcggcacag caagatcc                                         18

<210> SEQ ID NO 20
<211> LENGTH: 16
<212> TYPE: DNA
<213> ORGANISM: Artificial Sequence
<220> FEATURE:
<223> OTHER INFORMATION: Primer

<400> SEQUENCE: 20
ccgacagccg catcga                                           16

<210> SEQ ID NO 21
<211> LENGTH: 16
<212> TYPE: DNA
<213> ORGANISM: Artificial Sequence
<220> FEATURE:
<223> OTHER INFORMATION: Primer

<400> SEQUENCE: 21
ccgacagccg catcgg                                           16

<210> SEQ ID NO 22
<211> LENGTH: 18
<212> TYPE: DNA
<213> ORGANISM: Artificial Sequence
<220> FEATURE:
<223> OTHER INFORMATION: Primer

<400> SEQUENCE: 22
atcggcacag caagatcc                                         18

<210> SEQ ID NO 23
<211> LENGTH: 18
<212> TYPE: DNA

<210> SEQ ID NO 23
<211> LENGTH: 18
<212> TYPE: DNA
<213> ORGANISM: Artificial Sequence
<220> FEATURE:
<223> OTHER INFORMATION: Primer

<400> SEQUENCE: 23
cgacaaggcc agcaagat                                                 18

<210> SEQ ID NO 24
<211> LENGTH: 18
<212> TYPE: DNA
<213> ORGANISM: Artificial Sequence
<220> FEATURE:
<223> OTHER INFORMATION: Primer

<400> SEQUENCE: 24
cgacaaggcc agcaagac                                                 18

<210> SEQ ID NO 25
<211> LENGTH: 19
<212> TYPE: DNA
<213> ORGANISM: Artificial Sequence
<220> FEATURE:
<223> OTHER INFORMATION: Primer

<400> SEQUENCE: 25
cggtggtcct cctgagact                                                19

<210> SEQ ID NO 26
<211> LENGTH: 20
<212> TYPE: DNA
<213> ORGANISM: Artificial Sequence
<220> FEATURE:
<223> OTHER INFORMATION: Primer

<400> SEQUENCE: 26
caagacggtg aactggctct                                               20

<210> SEQ ID NO 27
<211> LENGTH: 19
<212> TYPE: DNA
<213> ORGANISM: Artificial Sequence
<220> FEATURE:
<223> OTHER INFORMATION: Primer

<400> SEQUENCE: 27
aagacggtga actggctcc                                                19

<210> SEQ ID NO 28
<211> LENGTH: 19
<212> TYPE: DNA
<213> ORGANISM: Artificial Sequence
<220> FEATURE:
<223> OTHER INFORMATION: Primer

<400> SEQUENCE: 28
cggtggtcct cctgagact                                                19

<210> SEQ ID NO 29
<211> LENGTH: 257
<212> TYPE: PRT
<213> ORGANISM: Sorghum bicolor

<400> SEQUENCE: 29

Met Pro Ser Thr Ala Met Ser Trp Asp Gly Tyr Gly Gly Gln Ile Phe
1               5                   10                  15

```
Pro Ala Asp Met Ser Ser Phe His His Gln Asp Thr Leu Glu Ala Val
            20                  25                  30

Phe Arg Gln Pro Glu Thr Thr Ala Pro Leu Gln Ala Pro Ala Ala Ala
        35                  40                  45

Gly Glu Met Glu Leu Leu Leu Arg Asn Gly Ser Pro Val Pro Val Val
    50                  55                  60

Asp Ala Gly Val His Ala Ala Ala Pro Arg Lys Arg Pro Phe Arg
65                  70                  75                  80

Thr Asp Arg His Ser Lys Ile Arg Thr Ala Gln Gly Val Arg Asp Arg
                85                  90                  95

Arg Met Arg Leu Ser Val Gly Val Ala Arg Glu Phe Phe Ala Leu Gln
            100                 105                 110

Asp Arg Leu Gly Phe Asp Lys Ala Ser Lys Thr Val Asn Trp Leu Leu
        115                 120                 125

Thr Gln Ser Lys Pro Ala Ile Asp Arg Leu Val Asp Ala Ala Glu Pro
    130                 135                 140

Ala Val Ala Leu Val Ser Gly Gly Pro Thr Val Val Lys Gly Arg
145                 150                 155                 160

Gly Glu Gly Asn Ser Ser Thr Cys Cys Leu Thr Val Asp Ser Arg
                165                 170                 175

Glu Glu Ala Thr Glu Lys Ala Arg Ser Arg Gly Gly Gly Gly Gly
            180                 185                 190

Thr Gly Gly Pro Asp Gly Pro Pro Ala Leu Met Glu His Gly Arg
        195                 200                 205

Gly Glu Leu Gly Trp Ile Met Thr Glu Ala Thr Ala Ala Ala Ala
    210                 215                 220

Ala Thr Ala Gln Pro Gln Gln Met Asp Gly Leu Glu Tyr Tyr Tyr Gln
225                 230                 235                 240

Tyr Cys Leu Gln Leu Glu Glu Met Met Arg Cys Asn Gly Gly Met Pro
                245                 250                 255

Arg

<210> SEQ ID NO 30
<211> LENGTH: 257
<212> TYPE: PRT
<213> ORGANISM: Sorghum bicolor

<400> SEQUENCE: 30

Met Pro Ser Thr Ala Met Ser Trp Asp Gly Tyr Gly Gly Gln Ile Phe
1               5                   10                  15

Pro Ala Asp Met Ser Ser Phe His His Gln Asp Thr Leu Glu Ala Val
            20                  25                  30

Phe Arg Gln Pro Glu Thr Thr Ala Pro Leu Gln Ala Pro Ala Ala Ala
        35                  40                  45

Gly Glu Met Glu Leu Leu Leu Arg Asn Gly Ser Pro Val Pro Val Val
    50                  55                  60

Asp Ala Gly Val His Ala Ala Ala Pro Arg Lys Gln Pro Phe Arg
65                  70                  75                  80

Thr Asp Arg His Ser Lys Ile Arg Thr Ala Gln Gly Val Arg Asp Arg
                85                  90                  95

Arg Met Arg Leu Ser Val Gly Val Ala Arg Glu Phe Phe Ala Leu Gln
            100                 105                 110

Asp Arg Leu Gly Phe Asp Lys Ala Ser Lys Thr Val Asn Trp Leu Leu
        115                 120                 125
```

Thr Gln Ser Lys Pro Ala Ile Asp Arg Leu Val Asp Ala Ala Glu Pro
    130                 135                 140

Ala Val Ala Leu Val Ser Gly Gly Pro Pro Thr Val Val Lys Gly Arg
145                 150                 155                 160

Gly Glu Gly Asn Ser Ser Thr Cys Cys Leu Thr Val Asp Ser Arg
                165                 170                 175

Glu Glu Ala Thr Glu Lys Ala Arg Ser Arg Gly Gly Gly Gly Gly
            180                 185                 190

Thr Gly Gly Pro Asp Gly Pro Pro Ala Leu Met Glu Glu His Gly Arg
        195                 200                 205

Gly Glu Leu Gly Trp Ile Met Thr Glu Ala Thr Ala Ala Ala Ala
    210                 215                 220

Ala Thr Ala Gln Pro Gln Gln Met Asp Gly Leu Glu Tyr Tyr Tyr Gln
225                 230                 235                 240

Tyr Cys Leu Gln Leu Glu Glu Met Met Arg Cys Asn Gly Gly Met Pro
                245                 250                 255

Arg

<210> SEQ ID NO 31
<211> LENGTH: 257
<212> TYPE: PRT
<213> ORGANISM: Sorghum bicolor

<400> SEQUENCE: 31

Met Pro Ser Thr Ala Met Ser Trp Asp Gly Tyr Gly Gly Gln Ile Phe
1               5                   10                  15

Pro Ala Asp Met Ser Ser Phe His His Gln Asp Thr Leu Glu Ala Val
            20                  25                  30

Phe Arg Gln Pro Glu Thr Thr Ala Pro Leu Gln Ala Pro Ala Ala Ala
        35                  40                  45

Gly Glu Met Glu Leu Leu Leu Arg Asn Gly Ser Pro Val Pro Val Val
    50                  55                  60

Asp Ala Gly Val His Ala Ala Ala Pro Arg Lys Arg Pro Phe Arg
65                  70                  75                  80

Thr Asn Arg His Ser Lys Ile Arg Thr Ala Gln Gly Val Arg Asp Arg
                85                  90                  95

Arg Met Arg Leu Ser Val Gly Val Ala Arg Glu Phe Phe Ala Leu Gln
            100                 105                 110

Asp Arg Leu Gly Phe Asp Lys Ala Ser Lys Thr Val Asn Trp Leu Leu
        115                 120                 125

Thr Gln Ser Lys Pro Ala Ile Asp Arg Leu Val Asp Ala Ala Glu Pro
    130                 135                 140

Ala Val Ala Leu Val Ser Gly Gly Pro Pro Thr Val Val Lys Gly Arg
145                 150                 155                 160

Gly Glu Gly Asn Ser Ser Thr Cys Cys Leu Thr Val Asp Ser Arg
                165                 170                 175

Glu Glu Ala Thr Glu Lys Ala Arg Ser Arg Gly Gly Gly Gly Gly
            180                 185                 190

Thr Gly Gly Pro Asp Gly Pro Pro Ala Leu Met Glu Glu His Gly Arg
        195                 200                 205

Gly Glu Leu Gly Trp Ile Met Thr Glu Ala Thr Ala Ala Ala Ala
    210                 215                 220

Ala Thr Ala Gln Pro Gln Gln Met Asp Gly Leu Glu Tyr Tyr Tyr Gln
225                 230                 235                 240

Tyr Cys Leu Gln Leu Glu Glu Met Met Arg Cys Asn Gly Gly Met Pro
            245                 250                 255

Arg

<210> SEQ ID NO 32
<211> LENGTH: 257
<212> TYPE: PRT
<213> ORGANISM: Sorghum bicolor

<400> SEQUENCE: 32

Met Pro Ser Thr Ala Met Ser Trp Asp Gly Tyr Gly Gly Gln Ile Phe
1               5                   10                  15

Pro Ala Asp Met Ser Ser Phe His His Gln Asp Thr Leu Glu Ala Val
            20                  25                  30

Phe Arg Gln Pro Glu Thr Thr Ala Pro Leu Gln Ala Pro Ala Ala Ala
        35                  40                  45

Gly Glu Met Glu Leu Leu Leu Arg Asn Gly Ser Pro Val Pro Val Val
50                  55                  60

Asp Ala Gly Val His Ala Ala Ala Pro Arg Lys Arg Pro Phe Arg
65                  70                  75                  80

Thr Asp Arg His Ser Lys Ile Arg Thr Ala Gln Gly Val Arg Asp Arg
                85                  90                  95

Trp Met Arg Leu Ser Val Gly Val Ala Arg Glu Phe Phe Ala Leu Gln
            100                 105                 110

Asp Arg Leu Gly Phe Asp Lys Ala Ser Lys Thr Val Asn Trp Leu Leu
        115                 120                 125

Thr Gln Ser Lys Pro Ala Ile Asp Arg Leu Val Asp Ala Ala Glu Pro
130                 135                 140

Ala Val Ala Leu Val Ser Gly Pro Pro Thr Val Val Lys Gly Arg
145                 150                 155                 160

Gly Glu Gly Asn Ser Ser Ser Thr Cys Cys Leu Thr Val Asp Ser Arg
                165                 170                 175

Glu Glu Ala Thr Glu Lys Ala Arg Ser Arg Gly Gly Gly Gly Gly
            180                 185                 190

Thr Gly Gly Pro Asp Gly Pro Pro Ala Leu Met Glu Glu His Gly Arg
        195                 200                 205

Gly Glu Leu Gly Trp Ile Met Thr Glu Ala Thr Ala Ala Ala Ala
210                 215                 220

Ala Thr Ala Gln Pro Gln Gln Met Asp Gly Leu Glu Tyr Tyr Tyr Gln
225                 230                 235                 240

Tyr Cys Leu Gln Leu Glu Glu Met Met Arg Cys Asn Gly Gly Met Pro
            245                 250                 255

Arg

<210> SEQ ID NO 33
<211> LENGTH: 257
<212> TYPE: PRT
<213> ORGANISM: Sorghum bicolor

<400> SEQUENCE: 33

Met Pro Ser Thr Ala Met Ser Trp Asp Gly Tyr Gly Gly Gln Ile Phe
1               5                   10                  15

Pro Ala Asp Met Ser Ser Phe His His Gln Asp Thr Leu Glu Ala Val
            20                  25                  30

Phe Arg Gln Pro Glu Thr Thr Ala Pro Leu Gln Ala Pro Ala Ala Ala
        35                  40                  45

```
Gly Glu Met Glu Leu Leu Arg Asn Gly Ser Pro Val Pro Val Val
 50                  55                  60

Asp Ala Gly Val His Ala Ala Ala Pro Arg Lys Arg Pro Phe Arg
 65                  70                  75                  80

Thr Asp Arg His Ser Lys Ile Arg Thr Ala Gln Gly Val Arg Asp Arg
                 85                  90                  95

Gln Met Arg Leu Ser Val Gly Val Ala Arg Glu Phe Phe Ala Leu Gln
                100                 105                 110

Asp Arg Leu Gly Phe Asp Lys Ala Ser Lys Thr Val Asn Trp Leu Leu
                115                 120                 125

Thr Gln Ser Lys Pro Ala Ile Asp Arg Leu Val Asp Ala Ala Glu Pro
                130                 135                 140

Ala Val Ala Leu Val Ser Gly Gly Pro Pro Thr Val Val Lys Gly Arg
145                 150                 155                 160

Gly Glu Gly Asn Ser Ser Ser Thr Cys Cys Leu Thr Val Asp Ser Arg
                165                 170                 175

Glu Glu Ala Thr Glu Lys Ala Arg Ser Arg Gly Gly Gly Gly Gly Gly
                180                 185                 190

Thr Gly Gly Pro Asp Gly Pro Pro Ala Leu Met Glu Glu His Gly Arg
                195                 200                 205

Gly Glu Leu Gly Trp Ile Met Thr Glu Ala Thr Ala Ala Ala Ala
210                 215                 220

Ala Thr Ala Gln Pro Gln Gln Met Asp Gly Leu Glu Tyr Tyr Tyr Gln
225                 230                 235                 240

Tyr Cys Leu Gln Leu Glu Glu Met Met Arg Cys Asn Gly Gly Met Pro
                245                 250                 255

Arg

<210> SEQ ID NO 34
<211> LENGTH: 257
<212> TYPE: PRT
<213> ORGANISM: Sorghum bicolor

<400> SEQUENCE: 34

Met Pro Ser Thr Ala Met Ser Trp Asp Gly Tyr Gly Gly Gln Ile Phe
 1               5                  10                  15

Pro Ala Asp Met Ser Ser Phe His His Gln Asp Thr Leu Glu Ala Val
                 20                  25                  30

Phe Arg Gln Pro Glu Thr Thr Ala Pro Leu Gln Ala Pro Ala Ala Ala
             35                  40                  45

Gly Glu Met Glu Leu Leu Arg Asn Gly Ser Pro Val Pro Val Val
 50                  55                  60

Asp Ala Gly Val His Ala Ala Ala Pro Arg Lys Arg Pro Phe Arg
 65                  70                  75                  80

Thr Asp Arg His Ser Lys Ile Arg Thr Ala Gln Gly Val Arg Asp Arg
                 85                  90                  95

Arg Met Arg Leu Ser Val Gly Val Ala Arg Glu Phe Phe Ala Leu Gln
                100                 105                 110

Asp Arg Leu Gly Phe Asp Lys Ala Ser Lys Met Val Asn Trp Leu Leu
                115                 120                 125

Thr Gln Ser Lys Pro Ala Ile Asp Arg Leu Val Asp Ala Ala Glu Pro
                130                 135                 140

Ala Val Ala Leu Val Ser Gly Gly Pro Pro Thr Val Val Lys Gly Arg
145                 150                 155                 160
```

```
Gly Glu Gly Asn Ser Ser Ser Thr Cys Cys Leu Thr Val Asp Ser Arg
                165                 170                 175

Glu Glu Ala Thr Glu Lys Ala Arg Ser Arg Gly Gly Gly Gly Gly Gly
            180                 185                 190

Thr Gly Gly Pro Asp Gly Pro Pro Ala Leu Met Glu Glu His Gly Arg
        195                 200                 205

Gly Glu Leu Gly Trp Ile Met Thr Glu Ala Thr Ala Ala Ala Ala Ala
    210                 215                 220

Ala Thr Ala Gln Pro Gln Gln Met Asp Gly Leu Glu Tyr Tyr Tyr Gln
225                 230                 235                 240

Tyr Cys Leu Gln Leu Glu Glu Met Met Arg Cys Asn Gly Gly Met Pro
                245                 250                 255

Arg

<210> SEQ ID NO 35
<211> LENGTH: 257
<212> TYPE: PRT
<213> ORGANISM: Sorghum bicolor

<400> SEQUENCE: 35

Met Pro Ser Thr Ala Met Ser Trp Asp Gly Tyr Gly Gly Gln Ile Phe
1               5                   10                  15

Pro Ala Asp Met Ser Ser Phe His His Gln Asp Thr Leu Glu Ala Val
            20                  25                  30

Phe Arg Gln Pro Glu Thr Thr Ala Pro Leu Gln Ala Pro Ala Ala Ala
        35                  40                  45

Gly Glu Met Glu Leu Leu Leu Arg Asn Gly Ser Pro Val Pro Val Val
50                  55                  60

Asp Ala Gly Val His Ala Ala Ala Pro Arg Lys Arg Pro Phe Arg
65                  70                  75                  80

Thr Asp Arg His Ser Lys Ile Arg Thr Ala Gln Gly Val Arg Asp Arg
                85                  90                  95

Arg Met Arg Leu Ser Val Gly Val Ala Arg Glu Phe Phe Ala Leu Gln
            100                 105                 110

Asp Arg Leu Gly Phe Asp Lys Ala Ser Lys Thr Val Asn Trp Leu Leu
        115                 120                 125

Thr Gln Ser Lys Pro Ala Ile Asp Arg Phe Val Asp Ala Ala Glu Pro
    130                 135                 140

Ala Val Ala Leu Val Ser Gly Pro Pro Thr Val Val Lys Gly Arg
145                 150                 155                 160

Gly Glu Gly Asn Ser Ser Ser Thr Cys Cys Leu Thr Val Asp Ser Arg
                165                 170                 175

Glu Glu Ala Thr Glu Lys Ala Arg Ser Arg Gly Gly Gly Gly Gly Gly
            180                 185                 190

Thr Gly Gly Pro Asp Gly Pro Pro Ala Leu Met Glu Glu His Gly Arg
        195                 200                 205

Gly Glu Leu Gly Trp Ile Met Thr Glu Ala Thr Ala Ala Ala Ala Ala
    210                 215                 220

Ala Thr Ala Gln Pro Gln Gln Met Asp Gly Leu Glu Tyr Tyr Tyr Gln
225                 230                 235                 240

Tyr Cys Leu Gln Leu Glu Glu Met Met Arg Cys Asn Gly Gly Met Pro
                245                 250                 255

Arg
```

```
<210> SEQ ID NO 36
<211> LENGTH: 212
<212> TYPE: PRT
<213> ORGANISM: Sorghum bicolor

<400> SEQUENCE: 36

Met Pro Ser Thr Ala Met Ser Trp Asp Gly Tyr Gly Gly Gln Ile Phe
1               5                   10                  15

Pro Ala Asp Met Ser Ser Phe His His Gln Asp Thr Leu Glu Ala Val
            20                  25                  30

Phe Arg Gln Pro Glu Thr Thr Ala Pro Leu Gln Ala Pro Ala Ala Ala
        35                  40                  45

Gly Glu Met Glu Leu Leu Leu Arg Asn Gly Ser Pro Val Pro Val Val
    50                  55                  60

Asp Ala Gly Val His Ala Ala Ala Pro Arg Lys Arg Pro Phe Arg
65                  70                  75                  80

Thr Asp Arg His Ser Lys Ile Arg Thr Ala Gln Gly Val Arg Asp Arg
                85                  90                  95

Arg Met Arg Leu Ser Val Gly Val Ala Arg Glu Phe Phe Ala Leu Gln
            100                 105                 110

Asp Arg Leu Gly Phe Asp Lys Ala Ser Lys Thr Val Asn Trp Leu Leu
        115                 120                 125

Thr Gln Ser Lys Pro Ala Ile Asp Arg Leu Val Asp Ala Ala Glu Pro
    130                 135                 140

Ala Val Ala Leu Val Ser Gly Gly Pro Pro Thr Val Val Lys Gly Arg
145                 150                 155                 160

Gly Glu Gly Asn Ser Ser Ser Thr Cys Cys Leu Thr Val Asp Ser Arg
                165                 170                 175

Glu Glu Ala Thr Glu Lys Ala Arg Ser Arg Gly Gly Gly Gly Gly Gly
            180                 185                 190

Thr Gly Gly Pro Asp Gly Pro Pro Ala Leu Met Glu Glu His Gly Arg
        195                 200                 205

Gly Glu Leu Gly
    210
```